(12) United States Patent
Callas et al.

(10) Patent No.: US 9,700,368 B2
(45) Date of Patent: Jul. 11, 2017

(54) SYSTEM AND METHOD FOR ELECTRICALLY ABLATING TISSUE OF A PATIENT

(75) Inventors: Peter Callas, Castro Valley, CA (US);
David Warden, Belmont, CA (US);
Robert M. Pearson, San Jose, CA (US)

(73) Assignee: AngioDynamics, Inc.

( * ) Notice: Subject to any disclaimer, the term of this patent is extended or adjusted under 35 U.S.C. 154(b) by 1095 days.

(21) Appl. No.: 13/273,001

(22) Filed: Oct. 13, 2011

(65) Prior Publication Data
US 2012/0095459 A1    Apr. 19, 2012

Related U.S. Application Data

(60) Provisional application No. 61/392,905, filed on Oct. 13, 2010.

(51) Int. Cl.
*A61B 18/00* (2006.01)
*A61B 18/14* (2006.01)
*A61B 34/00* (2016.01)

(52) U.S. Cl.
CPC .............. *A61B 18/14* (2013.01); *A61B 34/25* (2016.02); *A61B 2018/0016* (2013.01); *A61B 2018/00577* (2013.01); *A61B 2018/00613* (2013.01); *A61B 2018/00642* (2013.01); *A61B 2018/143* (2013.01)

(58) Field of Classification Search
CPC . A61B 18/14; A61B 19/56; A61B 2018/0016; A61B 2018/00577; A61B 2018/143; A61B 2018/00613; A61B 2018/00642; A61B 34/25

USPC ......... 606/27, 32, 34, 41; 607/27, 32, 34, 41
See application file for complete search history.

(56) References Cited

U.S. PATENT DOCUMENTS

| | | | |
|---|---|---|---|
| 1,653,819 | A | 12/1927 | Northcott et al. |
| 4,016,886 | A | 4/1977 | Doss |
| 4,226,246 | A | 10/1980 | Fragnet |
| 4,262,672 | A | 4/1981 | Kief |
| 4,407,943 | A | 10/1983 | Cole et al. |
| 4,810,963 | A | 3/1989 | Blake-Coleman et al. |
| 4,907,601 | A | 3/1990 | Frick |
| 4,946,793 | A | 8/1990 | Marshall, III |
| 5,019,034 | A | 5/1991 | Weaver et al. |

(Continued)

FOREIGN PATENT DOCUMENTS

| | | |
|---|---|---|
| DE | 863111 | 1/1953 |
| DE | 4000893 | 7/1991 |

(Continued)

OTHER PUBLICATIONS

Davalos, Rafael V., L. M. Mir, and B. Rubinsky. "Tissue ablation with irreversible electroporation." Annals of biomedical engineering 33.2 (2005): 223-231.*

(Continued)

*Primary Examiner* — Lindsey G Wehrheim
(74) *Attorney, Agent, or Firm* — Zachary F. Madonna

(57) ABSTRACT

System for electrically ablating tissue of a patient through a plurality of electrodes includes a memory, a processor and a treatment control module stored in the memory and executable by the processor. The treatment control module generates an estimated treatment region based on the number of electrical pulses to be applied.

16 Claims, 9 Drawing Sheets

(56) References Cited

U.S. PATENT DOCUMENTS

| | | |
|---|---|---|
| 5,052,391 A | 10/1991 | Silberstone et al. |
| 5,058,605 A | 10/1991 | Slovak |
| 5,098,843 A | 3/1992 | Calvin |
| 5,134,070 A | 7/1992 | Casnig |
| 5,173,158 A | 12/1992 | Schmukler |
| 5,193,537 A | 3/1993 | Freeman |
| 5,273,525 A | 12/1993 | Hofmann |
| 5,283,194 A | 2/1994 | Schmukler |
| 5,318,563 A | 6/1994 | Malis et al. |
| 5,328,451 A | 7/1994 | Davis et al. |
| 5,389,069 A | 2/1995 | Weaver |
| 5,403,311 A | 4/1995 | Abele et al. |
| 5,425,752 A | 6/1995 | Vu'Nguyen |
| 5,439,440 A | 8/1995 | Hofmann |
| 5,458,625 A | 10/1995 | Kendall |
| 5,533,999 A | 7/1996 | Hood et al. |
| 5,536,240 A | 7/1996 | Edwards et al. |
| 5,575,811 A | 11/1996 | Reid et al. |
| 5,626,146 A | 5/1997 | Barber et al. |
| 5,634,899 A | 6/1997 | Shapland et al. |
| 5,674,267 A | 10/1997 | Mir et al. |
| 5,702,359 A | 12/1997 | Hofmann |
| 5,720,921 A | 2/1998 | Meserol |
| 5,778,894 A | 7/1998 | Dorogi et al. |
| 5,782,882 A | 7/1998 | Lerman et al. |
| 5,800,378 A | 9/1998 | Edwards et al. |
| 5,810,762 A | 9/1998 | Hofmann |
| 5,836,905 A | 11/1998 | Lemelson et al. |
| 5,843,026 A | 12/1998 | Edwards et al. |
| 5,873,849 A | 2/1999 | Bernard |
| 5,919,142 A | 7/1999 | Boone et al. |
| 5,947,889 A | 9/1999 | Hehrlein |
| 5,983,131 A | 11/1999 | Weaver et al. |
| 5,991,697 A | 11/1999 | Nelson et al. |
| 5,999,847 A | 12/1999 | Elstrom |
| 6,009,347 A | 12/1999 | Hofmann |
| 6,010,613 A | 1/2000 | Walters et al. |
| 6,016,452 A | 1/2000 | Kasevich |
| 6,041,252 A | 3/2000 | Walker et al. |
| 6,055,453 A | 4/2000 | Hofmann et al. |
| 6,068,650 A | 5/2000 | Nanda et al. |
| 6,085,115 A | 7/2000 | Weaver et al. |
| 6,090,106 A | 7/2000 | Goble et al. |
| 6,102,885 A | 8/2000 | Bass |
| 6,106,521 A | 8/2000 | Blewett et al. |
| 6,109,270 A | 8/2000 | Mah et al. |
| 6,122,599 A | 9/2000 | Mehta |
| 6,132,419 A | 10/2000 | Hofmann |
| 6,159,163 A | 12/2000 | Strauss et al. |
| 6,208,893 B1 | 3/2001 | Hofmann |
| 6,210,402 B1 | 4/2001 | Olsen et al. |
| 6,212,433 B1 | 4/2001 | Behl |
| 6,216,034 B1 | 4/2001 | Hofmann |
| 6,219,577 B1 | 4/2001 | Brown et al. |
| 6,241,702 B1 | 6/2001 | Lundquist et al. |
| 6,261,831 B1 | 7/2001 | Agee |
| 6,278,895 B1 | 8/2001 | Bernard |
| 6,300,108 B1 | 10/2001 | Rubinsky |
| 6,326,177 B1 | 12/2001 | Schoenbach et al. |
| 6,347,247 B1 | 2/2002 | Dev et al. |
| 6,349,233 B1 | 2/2002 | Adams |
| 6,351,674 B2 | 2/2002 | Silverstone |
| 6,387,671 B1 | 5/2002 | Rubinsky et al. |
| 6,403,348 B1 | 6/2002 | Rubinsky et al. |
| 6,470,211 B1 | 10/2002 | Ideker et al. |
| 6,482,619 B1 | 11/2002 | Rubinsky et al. |
| 6,493,592 B1 | 12/2002 | Leonard et al. |
| 6,500,173 B2 | 12/2002 | Underwood et al. |
| 6,526,320 B2 | 2/2003 | Mitchell |
| 6,530,922 B2 * | 3/2003 | Cosman ............ A61B 18/1477 606/32 |
| 6,562,604 B2 | 5/2003 | Rubinsky et al. |
| 6,607,529 B1 | 8/2003 | Jones et al. |
| 6,611,706 B2 | 8/2003 | Avrahami et al. |
| 6,613,211 B1 | 9/2003 | McCormick et al. |
| 6,627,421 B1 | 9/2003 | Unger et al. |
| 6,653,091 B1 | 11/2003 | Dunn et al. |
| 6,669,691 B1 | 12/2003 | Taimisto |
| 6,692,493 B2 | 2/2004 | McGovern et al. |
| 6,697,669 B2 | 2/2004 | Dev et al. |
| 6,697,670 B2 | 2/2004 | Chornenky et al. |
| 6,702,808 B1 | 3/2004 | Kreindel |
| 6,795,728 B2 | 9/2004 | Chornenky et al. |
| 6,801,804 B2 | 10/2004 | Miller et al. |
| 6,865,416 B2 | 3/2005 | Dev et al. |
| 6,892,099 B2 | 5/2005 | Jaafar et al. |
| 6,912,417 B1 | 6/2005 | Bernard et al. |
| 6,927,049 B2 | 8/2005 | Rubinsky et al. |
| 6,962,587 B2 | 11/2005 | Johnson et al. |
| 6,972,014 B2 | 12/2005 | Eum et al. |
| 6,994,706 B2 | 2/2006 | Chornenky et al. |
| 7,053,063 B2 | 5/2006 | Rubinsky et al. |
| 7,063,698 B2 | 6/2006 | Whayne et al. |
| 7,130,697 B2 | 10/2006 | Chornenky et al. |
| 7,211,083 B2 | 5/2007 | Chornenky et al. |
| 7,267,676 B2 | 9/2007 | Chornenky et al. |
| 2001/0044596 A1 | 11/2001 | Jaafar |
| 2002/0010491 A1 | 1/2002 | Schoenbach |
| 2002/0055731 A1 | 5/2002 | Atala et al. |
| 2002/0077676 A1 | 6/2002 | Schroeppel et al. |
| 2002/0099323 A1 | 7/2002 | Dev et al. |
| 2002/0138117 A1 | 9/2002 | Son |
| 2002/0193831 A1 | 12/2002 | Smith, III |
| 2003/0009110 A1 | 1/2003 | Tu et al. |
| 2003/0055420 A1 | 3/2003 | Kadhiresan et al. |
| 2003/0060856 A1 | 3/2003 | Chornenky et al. |
| 2003/0088189 A1 | 5/2003 | Tu et al. |
| 2003/0130711 A1 | 7/2003 | Pearson et al. |
| 2003/0170898 A1 | 9/2003 | Gundersen et al. |
| 2003/0208200 A1 | 11/2003 | Palanker et al. |
| 2003/0225360 A1 | 12/2003 | Eppstein et al. |
| 2004/0019371 A1 | 1/2004 | Jaafar et al. |
| 2004/0059389 A1 | 3/2004 | Chornenky et al. |
| 2004/0146877 A1 | 7/2004 | Diss et al. |
| 2004/0153057 A1 | 8/2004 | Davison |
| 2004/0230187 A1 | 11/2004 | Lee et al. |
| 2004/0243107 A1 | 12/2004 | Mackoviak |
| 2004/0267189 A1 | 12/2004 | Mavor et al. |
| 2005/0043726 A1 | 2/2005 | McHale et al. |
| 2005/0049541 A1 | 3/2005 | Behar et al. |
| 2005/0165393 A1 | 7/2005 | Eppstein |
| 2005/0171523 A1 | 8/2005 | Rubinsky et al. |
| 2005/0171574 A1 | 8/2005 | Rubinsky et al. |
| 2005/0182462 A1 | 8/2005 | Chornenky et al. |
| 2005/0261672 A1 | 11/2005 | Deem et al. |
| 2005/0288730 A1 | 12/2005 | Deem et al. |
| 2006/0015147 A1 | 1/2006 | Persson et al. |
| 2006/0025760 A1 | 2/2006 | Podhajsky |
| 2006/0079883 A1 | 4/2006 | Elmouelhi et al. |
| 2006/0121610 A1 | 6/2006 | Rubinsky et al. |
| 2006/0212078 A1 | 9/2006 | Demarais et al. |
| 2006/0217703 A1 | 9/2006 | Chornenky et al. |
| 2006/0264752 A1 | 11/2006 | Rubinsky et al. |
| 2007/0010805 A1* | 1/2007 | Fedewa et al. ............... 606/27 |
| 2007/0043345 A1 | 2/2007 | Davalos et al. |
| 2007/0118069 A1 | 5/2007 | Persson et al. |
| 2008/0015664 A1* | 1/2008 | Podhajsky ......... A61B 18/1477 607/99 |
| 2008/0052786 A1 | 2/2008 | Lin et al. |
| 2008/0300589 A1 | 12/2008 | Paul et al. |
| 2009/0198231 A1* | 8/2009 | Esser .................... A61N 1/327 606/41 |
| 2010/0004623 A1* | 1/2010 | Hamilton, Jr. ..... A61B 18/1492 604/501 |
| 2010/0250209 A1* | 9/2010 | Pearson ............ A61B 18/1206 703/2 |
| 2011/0144635 A1* | 6/2011 | Harper et al. .................. 606/34 |

FOREIGN PATENT DOCUMENTS

| | | |
|---|---|---|
| EP | 0378132 | 7/1990 |
| EP | 0935482 | 5/2005 |
| WO | 9639531 | 12/1996 |

(56) References Cited

FOREIGN PATENT DOCUMENTS

| WO | 0020554 | 4/2000 |
|---|---|---|
| WO | 0107583 | 2/2001 |
| WO | 0107584 | 2/2001 |
| WO | 0107585 | 2/2001 |
| WO | 0181533 | 11/2001 |
| WO | 2004037341 | 5/2004 |

OTHER PUBLICATIONS

Rubinsky, Boris, Gary Onik, and Paul Mikus. "Irreversible electroporation: a new ablation modality—clinical implications." Technology in cancer research & treatment 6.1 (2007): 37-48.*

Davalos, R. V., L. M. Mir, and B. Rubinsky. "Tissue ablation with irreversible electroporation." Annals of biomedical engineering 33.2 (2005): 223-231.*

PCT International Search Report for WO 2012/051433 mailed May 30, 2012.

Amasha, et al., Quantitative Assessment of Impedance Tomography for Temperature Measurements in Microwave Hyperthermia, *Clin. Phys. Physiol. Meas.*, 1998, Suppl. A, 49-53.

Andreason, Electroporation as a Technique for the Transfer of Macromolecules into Mammalian Cell Lines, *J. Tiss. Cult. Meth.*, 15:56-62, 1993.

Baker, et al., Calcium-Dependent Exocytosis in Bovine Adrenal Medullary Cells with Leaky Plasma Membranes, *Nature*, vol. 276, pp. 620-622, 1978.

Barber, Electrical Impedance Tomography Applied Potential Tomography, Advances in Biomedical Engineering, Beneken and Thevenin, eds., IOS Press, 1993.

Beebe, S.J., et al., Nanosecond pulsed electric field (nsPEF) effects on cells and tissues: apoptosis induction and tumor growth inhibition. PPPS-2001 Pulsed Power Plasma Science 2001, 28$^{th}$ IEEE International Conference on Plasma Science and 13$^{th}$ IEEE International Pulsed Power Conference, Digest of Technical Papers (Cat. No. 01CH37251). IEEE, Part vol. 1, 2001, pp. 211-215, vol. I, Piscataway, NJ, USA.

Blad, et al., Impedance Spectra of Tumour Tissue in Comparison with Normal Tissue; a Possible Clinical Application for Electrical Impedance Tomography, *Physiol. Meas.* 17 (1996) A105-A115.

Bown, S.G., Phototherapy of tumors. *World J. Surgery*, 1983. 7: p. 700-9.

BPH Management Strategies: Improving Patient Satisfaction, *Urology Times*, May 2001, vol. 29, Supplement 1.

Brown, et al., Blood Flow Imaging Using Electrical Impedance Tomography, *Clin. Phys. Physiol. Meas.*, 1992, vol. 13, Suppl. A, 175-179.

Chandrasekar, et al., Transurethral Needle Ablation of the Prostate (TUNA)—a Propsective Study, Six Year Follow Up, (Abstract), Presented at 2001 National Meeting, Anaheim, CA, Jun. 5, 2001.

Coates, C.W.,et al., "The Electrical Discharge of the Electric Eel, Electrophorous Electricus," Zoologica, 1937, 22(1), pp. 1-32.

Cook, et al., ACT3: A High-Speed, High-Precision Electrical Impedance Tomograph, *IEEE Transactions on Biomedical Engineering*, vol. 41, No. 8, Aug. 1994.

Cowley, Good News for Boomers, *Newsweek*, Dec. 30, 1996/Jan. 6, 1997.

Cox, et al., Surgical Treatment of Atrial Fibrillation: A Review, *Europace* (2004) 5, S20-S-29.

Crowley, Electrical Breakdown of Biomolecular Lipid Membranes as an Electromechanical Instability, *Biophysical Journal*, vol. 13, pp. 711-724, 1973.

Davalos, et al., Tissue Ablation with Irreversible Electroporation, *Annals of Biomedical Engineering*, vol. 33, No. 2, Feb. 2005.

Davalos, et al ., Theoretical Analysis of the Thermal Effects During In Vivo Tissue Electroporation, Bioelectrochemistry, vol. 61, pp. 99-107, 2003.

Davalos, et al., A Feasibility Study for Electrical Impedance Tomography as a Means to Monitor T issue Electroporation for Molecular Medicine, *IEEE Transactions on Biomedical Engineering*, vol. 49, No. 4, Apr. 2002.

Davalos, Real-Time Imaging for Molecular Medicine through Electrical Impedance Tomography of Electroporation, Dissertation for Ph.D. in Engineering-Mechanical Engineering, Graduate Division of University of California, Berkeley, 2002.

Dean, Nonviral Gene Transfer to Skeletal, Smooth, and Cardiac Muscle in Living Animals, *Am J. Physiol Cell Physiol* 289: 233-245, 2005.

Dev, et al., Sustained Local Delivery of Heparin to the Rabbit Arterial Wall with an Electroporation Catheter, *Catheterization and Cardiovascular Diagnosis*, Nov. 1998, vol. 45, No. 3, pp. 337-343.

Dev, et al., Medical Applications of Electroporation, *IEEE Transactions of Plasma Science*, vol. 28, No. 1, pp. 206-223, Feb. 2000.

Duraiswami, et al., Boundary Element Techniques for Efficient 2-D and 3-D Electrical Impedance Tomography, *Chemical Engineering Science*, vol. 52, No. 13, pp. 2185-2196, 1997.

Duraiswami, et al., Efficient 2D and 3D Electrical Impedance Tomography Using Dual Reciprocity Boundary Element Techniques, *Engineering Analysis with Boundary Elements* 22, (1998) 13-31.

Duraiswami, et al., Solution of Electrical Impedance Tomography Equations Using Boundary Element Methods, *Boundary Element Technology* XII, 1997, pp. 226-237.

Edd, J., et al., In-Vivo Results of a New Focal Tissue Ablation Technique: Irreversible Electroporaton, *IEEE Trans. Biomed. Eng.* 53 (2006) p. 1409-1415.

Erez, et al., Controlled Destruction and Temperature Distributions in Biological Tissues Subjected to Monoactive Electrocoagulation, *Transactions of the ASME: Journal of Mechanical Design*, vol. 102, Feb. 1980.

Foster, R.S., et al., High-intensity focused ultrasound in the treatment of prostatic disease. *Eur. Urol.*, 1993. 23: 44-7).

Fox, et al., Sampling Conductivity Images via MCMC, Mathematics Department, Auckland University, New Zealand, May 1997.

Gauger, et al., A Study of Dielectric Membrane Breakdown in the Fucus Egg, *J. Membrane Biol.*, vol. 48, No. 3, pp. 249-264, 1979.

Gehl, et al., In Vivo Electroporation of Skeletal Muscle: Threshold, Efficacy and Relation to Electric Field Distribution, *Biochimica et Biphysica Acta* 1428, 1999, pp. 233-240.

Gençer, et al., Electrical Impedance Tomography: Induced-Current Imaging Achieved with a Multiple Coil System, *IEEE Transactions on Biomedical Engineering*, vol. 43, No. 2, Feb. 1996.

Gilbert, et al., Novel Electrode Designs for Electrochemotherapy, *Biochimica et Biophysica Acta* 1334, 1997, pp. 9-14.

Gilbert, et al., The Use of Ultrasound Imaging for Monitoring Cryosurgery, Proceedings 6$^{th}$ Annual Conference, IEEE Engineering in Medicine and Biology, 107-111, 1984.

Glidewell, et al., The Use of Magnetic Resonance Imaging Data and the Inclusion of Anisotropic Regions in Electrical Impedance Tomography, *Biomed, Sci. Instrum.* 1993; 29: 251-7.

Gothelf, et al., Electrochemotherapy: Results of Cancer Treatment Using Enhanced Delivery of Bleomycin by Electroporation, *Cancer Treatment Reviews* 2003: 29: 371-387.

Griffiths, et al., A Dual-Frequency Electrical Impedance Tomography System, *Phys. Med. Biol.*, 1989, vol. 34, No. 10, pp. 1465-1476.

Griffiths, The Importance of Phase Measurement in Electrical Impedance Tomography, *Phys. Med. Biol.*, 1987, vol. 32, No. 11, pp. 1435-1444.

Griffiths, Tissue Spectroscopy with Electrical Impedance Tomography: Computer Simulations, *IEEE Transactions on Biomedical Engineering*, vol. 42, No. 9, Sep. 1995.

Gumerov, et al., The Dipole Approximation Method and Its Coupling with the Regular Boundary Element Method for Efficient Electrical Impedance Tomography, *Boundary Element Technology* XIII, 1999.

Hapala, Breaking the Barrier: Methods for Reversible Permeabilization of Cellular Membranes, *Critical Reviews in Biotechnology*, 17(2): 105-122, 1997.

Heller, et al., Clinical Applications of Electrochemotherapy, *Advanced Drug Delivery Reviews*, vol. 35, pp. 119-129, 1999.

(56) References Cited

OTHER PUBLICATIONS

Ho, et al., Electroporation of Cell Membranes: A Review, *Critical Reviews in Biotechnology*, 16(4): 349-362, 1996.
Holder, et al., Assessment and Calibration of a Low-Frequency System for Electrical Impedance Tomography (EIT), Optimized for Use in Imaging Brain Function in Ambulant Human Subjects, *Annals of the New York Academy of Science*, vol. 873, Issue 1, Electrical BI, pp. 512-519, 1999.
Huang, et al., Micro-Electroporation: Improving the Efficiency and Understanding of Electrical Permeabilization of Cells, *Biomedical Microdevices*, vol. 2, pp. 145-150, 1999.
Hughes, et al., An Analysis of Studies Comparing Electrical Impedance Tomography with X-Ray Videofluoroscopy in the Assessment of Swallowing, *Physiol. Meas.* 15, 1994, pp. A199-A209.
Issa, et al., The TUNA Procedure for BPH: Review of the Technology: The TUNA Procedure for BPH: Basic Procedure and Clinical Results, Reprinted from *Infections in Urology*, Jul./Aug. 1998 and Sep./Oct. 1998.
Ivanuša, et al., MRI Macromolecular Contrast Agents as Indicators of Changed Tumor Blood Flow, *Radiol. Oncol.* 2001; 35(2): 139-47.
Jaroszeski, et al., In Vivo Gene Delivery by Electroporation, *Advanced Drug Delivery Review*, vol. 35, pp. 131-137, 1999.
Kinosita, et al., Hemolysis of Human Erythrocytes by a Transient Electric Field, *Proc. Natl. Acad. Sci. USA*, vol. 74, No. 5, pp. 1923-1927, 1977.
Liu, et al., Measurement of Pharyngeal Transit Time by Electrical Impedance Tomography, *Clin. Phys. Physiol. Meas.*, 1992, vol. 13, Suppl. A, pp. 197-200.
Lundqvist, et al., Altering the Biochemical State of Individual Cultured Cells and Organelles with Ultramicroelectrodes, *Proc. Natl. Acad. Sci. USA*, vol. 95, pp. 10356-10360, Sep. 1998.
Lurquin, Gene Transfer by Electroporation, *Molecular Biotechnology*, vol. 7, 1997.
Lynn, et al., A New Method for the Generation and use of Focused Ultrasound in Experimental Biology, *The Journal of General Physiology*, vol. 26, 179-193, 1942.
Miklavčič, et al., A Validated Model of an in Vivo Electric Field Distribution in Tissues for Electrochemotherapy and for DNA Electrotransfer for Gene Therapy, *Biochimica et Biophysica Acta* 1523 (2000), pp. 73-83.
Miklavčič, et al., The Importance of Electric Field Distribution for Effective in Vivo Electroporation of Tissues, *Biophysical Journal*, vol. 74, May 1998, pp. 2152-2158.
Miller, L., et al., Cancer cells ablation with irreversible electroporation, *Technology in Cancer Research and Treatment* 4 (2005) 699-706.
Mir, Therapeutic Perspectives of In Vivo Cell Electropermeabilization, *Bioelectrochemistry*, vol. 53, pp. 1-10, 2000.
Mir, L.M., et al., Electric Pulse-Mediated Gene Delivery to Various Animal Tissues, in Advances in Genetics, Academic Press, 2005, p. 83-114.
Mir, L.M. and Orlowski, S., The basis of electrochemotherapy, in Electrochemotherapy, electrogenetherapy, and transdermal drug delivery: electrically mediated delivery of molecules to cells, M.J. Jaroszeski, R. Heller, R. Gilbert, Editors, 2000, Humana Press, p. 99-118.
Mir, et al., Effective Treatment of Cutaneous and Subcutaneous Malignant Tumours by Electrochemotherapy, *British Journal of Cancer*, vol. 77, No. 12, pp. 2336-2342, 1998.
Mir, et al., Electrochemotherapy Potentiation of Antitumour Effect of Bleomycin by Local Electric Pulses, *European Journal of Cancer*, vol. 27, No. 1, pp. 68-72, 1991.
Mir, et al., Electrochemotherapy, a Novel Antitumor Treatment: First Clinical Trial, *C.R. Acad. Sci. Paris*, Ser. III, vol. 313, pp. 613-618, 1991.
Narayan, et al., Establishment and Characterization of a Human Primary Prostatic Adenocarcinoma Cell Line (ND-1), *The Journal of Urology*, vol. 148, 1600-1604, Nov. 1992.

Naslund, Michael J., Transurethral Needle Ablation of the Prostate, *Urology*, vol. 50, No. 2, Aug. 1997.
Naslund, Cost-Effectiveness of Minimally Invasive Treatments and Transurethral Resection (TURP) in Benign Prostatic Hyperplasia (BPH), (Abstract), Presented at 2001 AUA National Meeting Anaheim, CA, Jun. 5, 2001.
Neumann, et al., Gene Transfer into Mouse Lyoma Cells by Electroporation in High Electric Fields, *J. Embo.*, vol. 1, No. 7, pp. 841-845, 1982.
Neumann, et al., Permeability Changes Induced by Electric Impulses in Vesicular Membranes, *J. Membrane Biol.*, vol. 10, pp. 279-290, 1972.
Okino, et al., Effects of High-Voltage Electrical Impulse and an Anticancer Drug on In Vivo Growing Tumors, *Japanese Journal of Cancer Research*, vol. 78, pp. 1319-1321, 1987.
Onik, et al., Sonographic Monitoring of Hepatic Cryosurgery in an Experimental Animal Model, *AJR American J. of Roentgenology*, vol. 144, pp. 1043-1047, May 1985.
Onik, et al., Ultrasonic Characteristics of Frozen Liver, *Cryobiology*, vol. 21, pp. 321-328, 1984.
Organ, L.W., Electrophysiological principles of radiofrequency lesion making, *Apply. Neurophysiol.*, 1976. 39: p. 69-76.
Piñero, et al., Apoptotic and Necrotic Cell Death Are Both Induced by Electroporation in HL60 Human Promyeloid Leukaemia Cells, *Apoptosis*, vol. 2, No. 3, 330-336, Aug. 1997.
Precision Office TUNA System, When Patient Satisfaction is Your Goal.
Rols, M.P., et al., Highly Efficient Transfection of Mammalian Cells by Electric Field Pulses: Application to Large Volumes of Cell Culture by Using a Flow System, *Eur. J. Biochem.* 1992, 206, pp. 115-121.
Rubinsky, B., ed, Cryosurgery. *Annu Rev. Biomed. Eng.* vol. 2 2000. 157-187.
Schmukler, Impedance Spectroscopy of Biological Cells, downloaded from IEEE Xplore website.
Sersa, et al., Reduced Blood Flow and Oxygenation in SA-1 Tumours after Electrochemotherapy with Cisplatin, *British Journal of Cancer*, 87, 1047-1054, 2002.
Sersa, et al., Tumour Blood Flow Modifying Effects of Electrochemotherapy: a Potential Vascular Targeted Mechanism, *Radiol. Oncol.*, 37(1): 43-8, 2003.
Sharma, et al., Poloxamer 188 Decreases Susceptibility of Artificial Lipid Membranes to Electroporation, *Biophysical Journal*, vol. 71, No. 6, pp. 3229-3241, Dec. 1996.
Shiina, S., et al, Percutaneous ethanol injection therapy for hepatocellular carcinoma: results in 146 patients. *AJR*, 1993, 160: p. 1023-8.
Thompson, et al., To determine whether the temperature of 2% lignocaine gel affects the initial discomfort which may be associated with its instillation into the male urethra, *BJU International* (1999), 84, 1035-1037.
TUNA—Suggested Local Anesthesia Guidelines.
Vidamed, Inc., Transurethral Needle Ablation (TUNA): Highlights from Worldwide Clinical Studies, Vidamed's Office TUNA System.
Weaver, Electroporation: A General Phenomenon for Manipulating Cells and Tissues, *Journal of Cellular Biochemistry*, 51: 426-435, 1993.
Weaver, et al., Theory of Electroporation: A Review, *Bioelectrochemistry and Bioenergetics*, vol. 41, pp. 136-160, 1996.
Zimmermann, et al., Dielectric Breakdown of Cell Membranes, *Biophysical Journal*, vol. 14, No. 11, pp. 881-899, 1974.
Zlotta, et al., Possible Mechanisms of Action of Transurethral Needle Ablation of the Prostate on Benign Prostatic Hyperplasia Symptoms: a Neurohistochemical Study, Reprinted from *Journal of Urology*, vol. 157, No. 3, Mar. 1997, pp. 894-899.
Zlotta, et al., Long-Term Evaluation of Transurethral Needle Ablation of the Prostate (TUNA) for Treatment of Benign Prostatic Hyperplasia (BPH): Clinical Outcome After 5 Years. (Abstract) Presented at 2001 AUA National Meeting, Anaheim, CA—Jun. 5, 2001.

\* cited by examiner

FIG. 4

SYSTEM AND METHOD FOR ELECTRICALLY ABLATING TISSUE OF A PATIENT

CROSS-REFERENCE TO RELATED APPLICATION

This application claims priority under 35 U.S.C. 119(e) to U.S. Provisional Application No. 61/392,905, filed Oct. 13, 2010, which is incorporated by reference herein.

This application is also related to PCT International Application Number PCT/US10/29243, filed Mar. 30, 2010 and entitled "System and Method for Estimating a Treatment Region for a Medical Treatment Device and for Interactively Planning a Treatment of a Patient" (hereinafter the "IRE Treatment Application"), which is incorporated herein by reference.

This application is also related to PCT International Application Number PCT/US10/36734, filed May 28, 2010 and entitled "System and Method for Synchronizing Energy Delivery to the Cardiac Rhythm", which is also incorporated herein by reference.

FIELD OF THE INVENTION

The present invention relates to a control system for controlling a medical treatment device. More particularly, the present application relates to a system and method for electrically ablating tissue of a patient.

BACKGROUND OF THE INVENTION

Devices for delivering therapeutic energy such as an ablation device using irreversible electroporation (IRE) include a pulse generator and one or more electrodes coupled to the generator. The pulse generator delivers the therapeutic energy to a targeted tissue through the electrodes, thereby causing ablation of the tissue.

Once a target treatment area/region is located within a patient, the electrodes of the device are placed in such a way as to create a treatment zone that surrounds the target treatment region.

Prior to treatment, a treatment planning system is used to generate an estimated treatment region that completely covers the target treatment region. The estimated region is used by a physician to plan where to place the electrodes in the patient.

This can be effective when the target area is relatively small, e.g., less than 2 cm in length. However, when the target area is much larger, e.g., larger than 3 cm in length, the physician is forced to use a large number of electrodes, e.g., 4 or more electrodes. This makes accurately placing the electrodes much more difficult as moving one electrode affects the spacing from all other electrodes.

Alternatively, the large target area can be divided into two or more smaller areas and the treatment procedure for one area can be repeated to cover the other divided areas. However, this makes the entire treatment procedure much longer. The longer procedure makes it riskier for the patient since the patient would have to stay on an operating table much longer with an exposed body portion to be treated. The longer procedure also makes the procedure more expensive.

Therefore, it would be desirable to provide a system and method for electrically ablating tissue of a patient more safely and efficiently.

SUMMARY OF THE DISCLOSURE

According to one aspect of the invention, a system for electrically ablating tissue of a patient through a plurality of electrodes is provided. The system includes a memory, a processor and a treatment control module stored in the memory and executable by the processor. The treatment control module generates an estimated treatment region by taking into account the relationship between the ablation size and the number of pulses to be applied. This allows treatment of relatively large target ablation regions more efficiently and accurately.

According to another aspect of the invention, a method of electrically ablating tissue of a patient through a plurality of electrodes is provided. The method includes receiving positions of a plurality of electrodes and generating an estimated treatment region based on the received electrode positions and the number of pulses to be applied.

BRIEF DESCRIPTION OF THE DRAWINGS

FIG. 4 is a screen shot of a "Probe Selection" screen of the treatment control module showing a side view and top view of the four probe array and an example of the general shape of the treatment zone that can be generated by a four probe array.

DETAILED DESCRIPTION OF INVENTION

Throughout the present teachings, any and all of the one, two, or more features and/or components disclosed or suggested herein, explicitly or implicitly, may be practiced and/or implemented in any combinations of two, three, or more thereof, whenever and wherever appropriate as understood by one of ordinary skill in the art. The various features and/or components disclosed herein are all illustrative for the underlying concepts, and thus are non-limiting to their actual descriptions. Any means for achieving substantially the same functions are considered as foreseeable alternatives and equivalents, and are thus fully described in writing and fully enabled. The various examples, illustrations, and embodiments described herein are by no means, in any degree or extent, limiting the broadest scopes of the claimed inventions presented herein or in any future applications claiming priority to the instant application.

Figure 1:
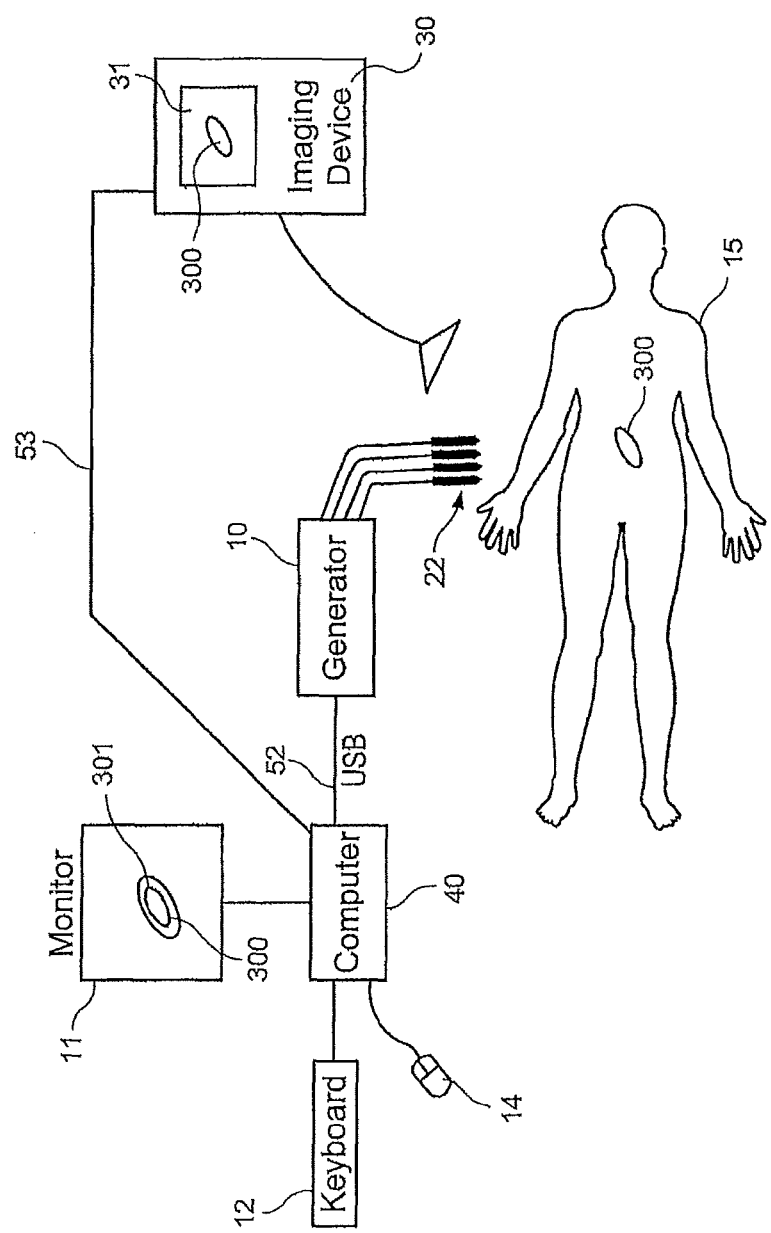
FIG. 1 illustrates several components of a medical treatment system to treat a patient according to the present invention.

One embodiment of the present invention is illustrated in FIG. 1. One or more probes/electrodes 22 deliver therapeutic energy and are powered by a voltage pulse generator 10 that generates high voltage pulses as therapeutic energy such as pulses capable of irreversibly electroporating the tissue cells. In the embodiment shown, the voltage pulse generator 10 includes six separate receptacles for receiving up to six individual probes 22 which are adapted to be plugged into the respective receptacle. The receptacles are each labeled with a number in consecutive order. In other embodiments, the voltage pulse generator can have any number of receptacles for receiving more or less than six probes.

In the embodiment shown, each probe 22 includes either a monopolar electrode or bipolar electrodes having two electrodes separated by an insulating sleeve. In one embodiment, if the probe includes a monopolar electrode, the amount of exposure of the active portion of the electrode can be adjusted by retracting or advancing an insulating sleeve relative to the electrode. See, for example, U.S. Pat. No. 7,344,533, which is incorporated by reference herein. The generator 10 is connected to a treatment control computer 40 having input devices such as keyboard 12 and a pointing device 14, and an output device such as a display device 11 for viewing an image of a target treatment region such as a lesion 300 surrounded by a safety margin 301. The pulse generator 10 is used to treat a lesion 300 inside a patient 15. An imaging device 30 includes a monitor 31 for viewing the lesion 300 inside the patient 15 in real time. Examples of imaging devices 30 include ultrasonic, CT, MRI and fluoroscopic devices as are known in the art.

The present invention includes computer software (treatment control module 54) which assists a user to plan for, execute, and review the results of a medical treatment procedure, as will be discussed in more detail below. For example, the treatment control module 54 assists a user to plan for a medical treatment procedure by enabling a user to more accurately position each of the probes 22 of the pulse generator 10 in relation to the lesion 300 in a way that will generate the most effective treatment zone. The treatment control module 54 can display the anticipated treatment zone based on the position of the probes and the treatment parameters. The treatment control module 54 can display the progress of the treatment in real time and can display the results of the treatment procedure after it is completed. This information can be used to determine whether the treatment was successful and whether it is necessary to re-treat the patient.

For purposes of this application, the terms "code", "software", "program", "application", "software code", "software module", "module" and "software program" are used interchangeably to mean software instructions that are executable by a processor.

The "user" can be a physician or other medical professional. The treatment control module 54 executed by a processor outputs various data including text and graphical data to the monitor 11 associated with the generator 10.

Figure 2:
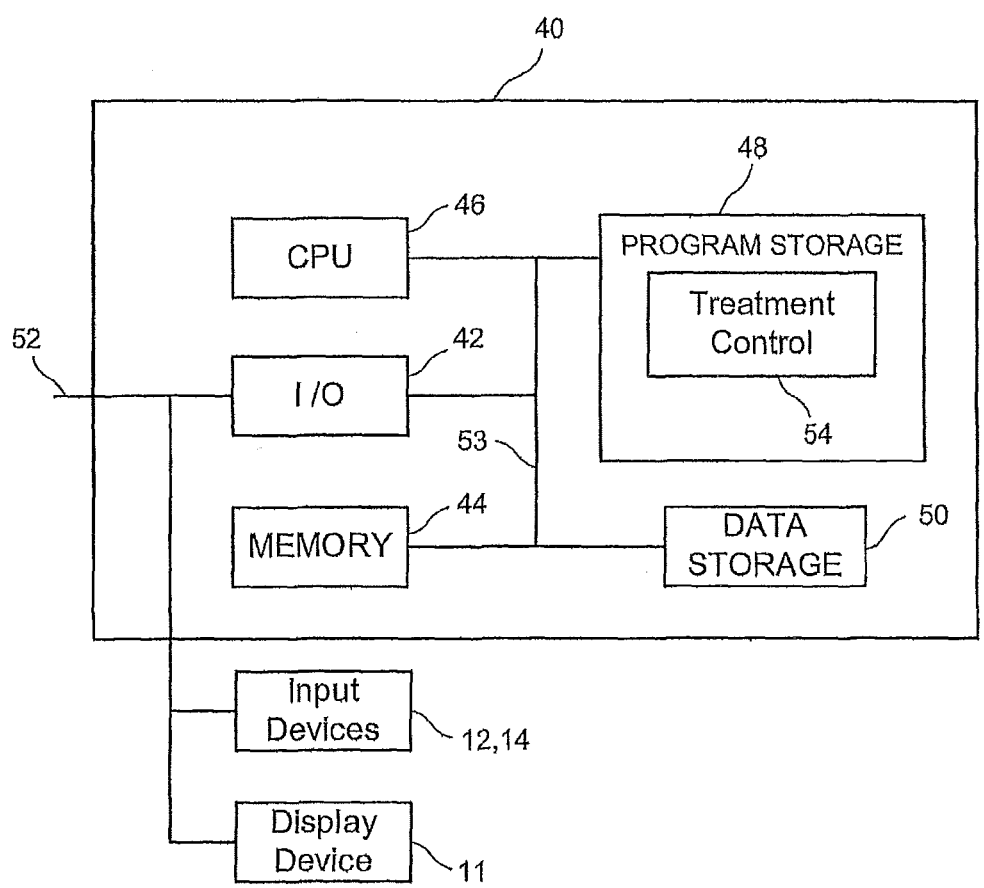
FIG. 2 is a schematic diagram of a treatment control computer of the present invention.

Referring now to FIG. 2, the treatment control computer 40 of the present invention manages planning of treatment for a patient. The computer 40 is connected to the communication link 52 through an I/O interface 42 such as a USB (universal serial bus) interface, which receives information from and sends information over the communication link 52 to the voltage generator 10. The computer 40 includes memory storage 44 such as RAM, processor (CPU) 46, program storage 48 such as ROM or EEPROM, and data storage 50 such as a hard disk, all commonly connected to each other through a bus 53. The program storage 48 stores, among others, a treatment control module 54 which includes a user interface module that interacts with the user in planning for, executing and reviewing the result of a treatment. Any of the software program modules in the program storage 48 and data from the data storage 50 can be transferred to the memory 44 as needed and is executed by the CPU 46.

In one embodiment, the computer 40 is built into the voltage generator 10. In another embodiment, the computer 40 is a separate unit which is connected to the voltage generator through the communication link 52. In a preferred embodiment, the communication link 52 is a USB link.

In one embodiment, the imaging device 30 is a stand alone device which is not connected to the computer 40. In the embodiment as shown in FIG. 1, the computer 40 is connected to the imaging device 30 through a communication link 53. As shown, the communication link 53 is a USB link. In this embodiment, the computer can determine the size and orientation of the lesion 300 by analyzing the data such as the image data received from the imaging device 30, and the computer 40 can display this information on the monitor 11. In this embodiment, the lesion image generated by the imaging device 30 can be directly displayed on the grid 200 of the monitor 11 of the computer running the treatment control module 54. This embodiment would provide an accurate representation of the lesion image on the grid 200, and may eliminate the step of manually inputting the dimensions of the lesion in order to create the lesion image on the grid 200. This embodiment would also be useful to provide an accurate representation of the lesion image if the lesion has an irregular shape.

The basic functionality of the computer software (treatment control module 54) will now be discussed in relation to the following example.

It should be noted that the software can be used independently of the generator 10. For example, the user can plan the treatment in a different computer as will be explained below and then save the treatment parameters to an external memory device, such as a USB flash drive (not shown). The data from the memory device relating to the treatment parameters can then be downloaded into the computer 40 to be used with the generator 10 for treatment.

Figure 3:
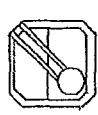
FIG. 3 is a screen shot of an "Information" screen of a treatment control module showing various input boxes.

After the treatment control module 54 is initialized, it displays an "Information" screen with various input boxes as shown in FIG. 3. A keyboard or other input device 12, together with a mouse or other pointing device 14 (see FIG. 1) are used to input the data. Any data that is inputted into the input boxes can be saved into internal or external memory along with a record of the treatment as described below for future reference. The basic patient information can be inputted, such as a patient ID number in input box 100, the name of the patient in input box 101, and the age of the patient in input box 102. The user can enter clinical data, such as the clinical indication of the treatment in input box 114. The date of the procedure is automatically displayed at 111 or can be inputted by the user in another embodiment. The user can enter other case information such as the name of the physician in input box 112 and any specific case notes in input box 113.

The dimensions of the lesion 300 are determined from viewing it on the monitor 31 of the imaging device 30 (see FIG. 1) such as an ultrasonic imaging device and using known methods to calculate the dimensions from the image generated from the imaging device 31. The dimensions of the lesion 300 (length at input box 103, width at input box 104, and depth at input box 105) are inputted into the program. A safety margin is selected at input box 106 which will surround the entire lesion 300 in three dimensions. According to the size of the safety margin that is selected, a target treatment region is automatically calculated and is displayed in boxes 107, 108, and 109 as shown. In one embodiment, the safety margin value may be set to zero. For example, when treating a benign tumor, a safety margin may not be necessary.

In the embodiment shown in FIG. 3, the user has indicated that the lesion that will be treated has a length of 2 cm, width of 1 cm and a depth of 1 cm. With a user specified margin of 1 cm (which is a default margin setting), the target treatment region has a length of 4 cm, width of 3 cm and a depth of 3 cm.

The user can select the "ECG synchronization" option by clicking the circle in the box 110 in order to synchronize the pulses with an electrocardiogram (ECG) device, if such a device is being used during the procedure. The other options available for treatment that are included in box 110 can include an option for "90 PPM" (pulses per minute) or "240 PPM". The user should select at least one of the three options provided in box 110. After all of the necessary data has been inputted, the user clicks on the "Next" button with a pointing device 14 to proceed to the next screen described below.

Further regarding the ECG synchronization option, if this circle is selected in window 110, the treatment control module 54 will test this functionality to verify that the system is working properly. The treatment control module 54 can automatically detect whether an error has occurred during the testing phase of the ECG feature. The detectable errors include, but are not limited to, "no signal" (such as no pulses for 3.5 seconds) and "noisy" (such as pulses occurring at a rate greater than 120 beats per minute for at least 3.5 seconds).

The treatment control module 54 can synchronize energy release with cardiac rhythm by analyzing cardiac output such as electrocardiogram results (or other cardiac function output) and sending synchronization signals to a controller of the pulse generator 10. The control module 54 is also capable of generating internal flags such as a synchronization problem flag and a synchronization condition flag to indicate to users on a graphic user interface a synchronization status, so that energy pulse delivery can be synchronized with the cardiac rhythm for each beat (in real-time) or aborted as necessary for patient safety and treatment efficiency.

Specifically, the control module 54 synchronizes energy pulses such as IRE (irreversible electroporation) pulses with a specific portion of the cardiac rhythm. The module uses the R-wave of the heartbeat and generates a control signal to the pulse generator 10 indicating that this portion of the heartbeat is optimal for release of IRE pulses. For clarity, the S wave would be an optimal time for delivery of an energy pulse, but due to the fact that the S wave ends nebulously in some cases, the R wave is used as an indicator to start timing of energy release.

More specifically, the synchronization feature of the control module 54 allows for monitoring of heart signals so as to ensure that changes, maladies, and other alterations associated with the heartbeat are coordinated such that pulses from the pulse generator 10 are released at the proper time, and that if the heartbeat is out of its normal rhythm, that the release of energy is either altered or aborted.

Next, the user can select the number of probes that the user believes will be necessary to produce a treatment zone which will adequately cover the lesion 300 and any safety margin 301. The selection is made by clicking the circle next to each type of device, as shown in the "Probe Selection" screen, illustrated in FIG. 4.

In one embodiment, a "Probes Selection Status" box 199 identifies which of the receptacles, if any, on the generator 10 have been connected to a probe by displaying the phrase "Connected" or the like next to the corresponding probe number. In one embodiment, each receptacle includes an RFID device and a connector for each probe which connects to the receptacle and includes a compatible RFID device, so that the treatment control module 54 can detect whether or not an authorized probe has been connected to the receptacle on the generator 10 by detecting a connection of the compatible RFID devices. If an authorized probe is not connected to a receptacle on the generator, the phrase "Not Connected" or the like will appear next to the probe number. In addition, the color of each probe shown in the "Probes Selection Status" box 199 can be used to indicate whether or not each receptacle on the generator is connected to a compatible probe. This feature allows the user to verify that the requisite number of probes are properly connected to the generator 10 before selecting a probe type for the treatment procedure. For example, if the treatment control module 54 detects a problem with the probe connection status (e.g. selecting a three probe array when only two probes are connected to the generator), it can notify the user by displaying an error message.

The user can select which of the connected probes will be used to perform the treatment procedure, by clicking on the box next to the selected probes in the "Probes Selection Status" box 199. By default the treatment control module 54 will automatically select probes in ascending numerical order, as they are labeled.

Figure 4:
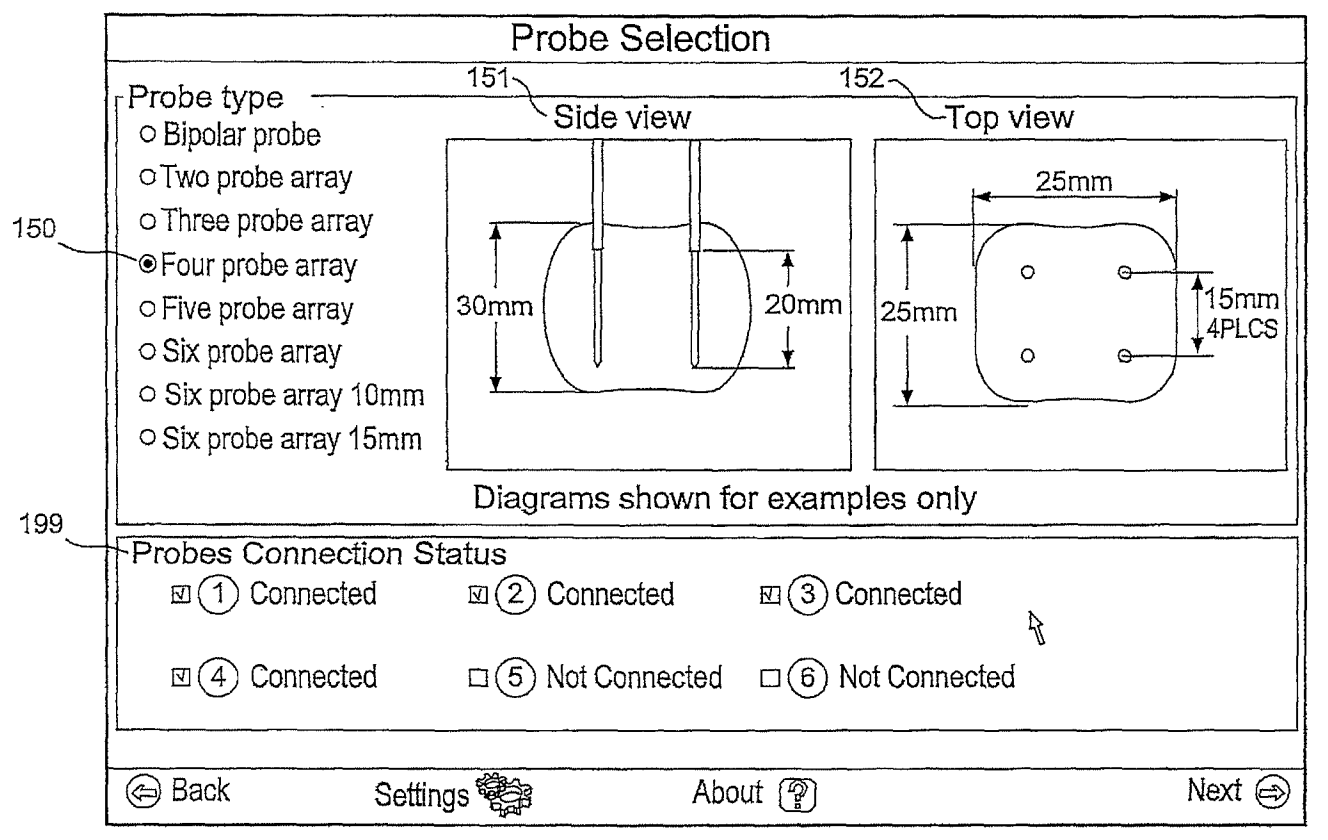

Referring to FIG. 4, circle 150 is used to select a four probe array. FIG. 4 illustrates a side view 151 and top view 152 of the four probe array and an example of the general shape of the treatment zone that can be generated by a four probe array. In the illustrated example, the exposed portion of each of the electrodes as shown is 20 mm in length and each pair of the four probes are equally spaced from each other by 15 mm, as measured at four places (PLCS) along the perimeter.

Figure 5:
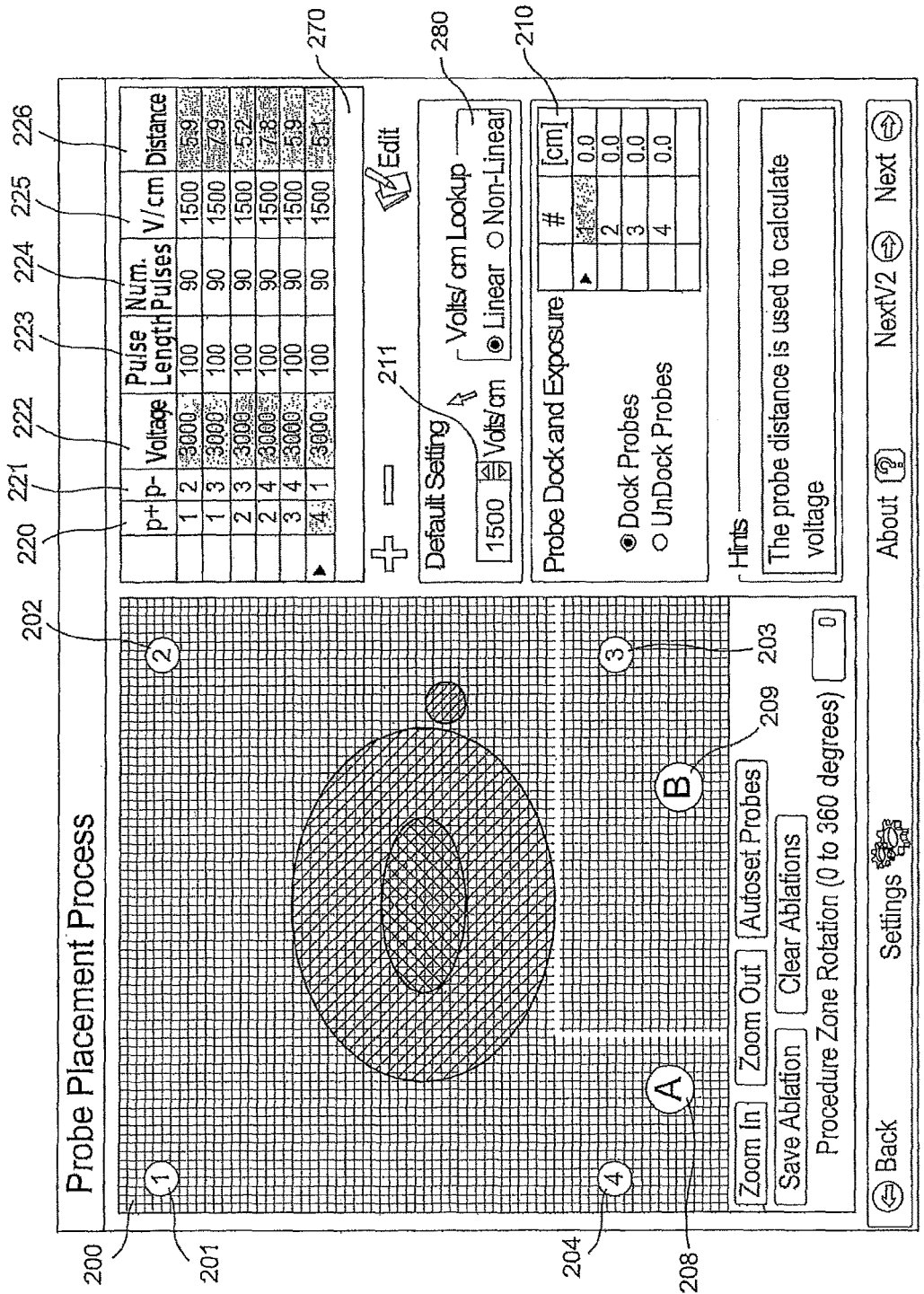
FIG. 5 is a screen shot of a "Probe Placement Process" screen of the treatment control module.

FIG. 5 illustrates a "Probe Placement Process" screen of one aspect of the invention. The screen illustrated by FIG. 5 shows a lesion 300 according to the dimensions which were inputted on the "Information" screen (see FIG. 3) along with a safety margin 301, if any, that was previously inputted. In the example depicted in FIG. 5, the lesion 300 has a length of 2.0 cm and a width of 1.0 cm, and the device selected on the "Probe Selection" screen (see FIG. 4) is a four probe array. The lesion 300 is displayed near the center of an x-y grid 200 with the distance between two adjacent grid lines representing 1 mm. Each of the four probes 201, 202, 203, 204 is displayed in the grid 200 and each probe can be manually positioned within the grid by clicking and dragging the probe with the pointing device 14. Two fiducials 208, 209 labeled "A" and "B", respectively, are also displayed on the grid 200 and are used as a point of reference or a measure as will be described below.

The amount of longitudinal exposure of the active electrode portion for each probe that has already been manually adjusted by the user as explained above can be manually inputted in input box 210, which can be selected by the user according to the depth (z) of the lesion. In this way, the treatment control module 54 can generate an estimated treatment zone according to the treatment parameters, and locations and depths of the probes. In one embodiment, a second x-z grid is displayed on the monitor 11 of the computer running the treatment control module 54. In one embodiment, the treatment control module 54 can automatically calculate preferred values for the amount of longitudinal exposure of the active electrode portions based on the size and shape of the lesion. The depth (z) of the electric field image can be calculated analytically or with interpolation and displayed on the x-z grid. Because the distribution of the electric field (i.e., expected treatment region) between two monopolar electrodes may "dip in" along the boundary line (e.g., a peanut shaped treatment region due to large spacing between the two electrodes where the width of the region is smaller in the middle; see for example region 305 in FIG. 9) depending on the electrode location and the applied voltage, it is beneficial to have an x-z grid included on the monitor. For example, if this "dip" of the boundary line travels into, rather than surround/cover, the lesion region, then the targeted region may not be fully treated. As a default to ensure treatment of the entire lesion region, the probe depth placement and the exposure length may be set unnecessarily higher to ensure erring on the safe side. However, this will potentially treat a much larger volume than needed, killing healthy surrounding tissue, which can be an issue when treating sensitive tissues such as the pancreas, brain, etc. By optimizing the treatment depth (z) together with the width (x) and height (y), this effect may be reduced, further enhancing procedural protocol and clinical outcome.

The probe dock status is indicated in box 210, by indicating if the probes are "docked" or "undocked". The "UnDock Probes" button allows the user to "unplug" the probes from the generator while the "Probe Placement Process" screen is displayed without causing error messages. In normal operation, the user plugs the probes into the generator on the "Probe Selection" screen, and then the probes are "authorized" as being compatible probes according to the RFID devices, as discussed above. When the user proceeds to the "Probe Placement Process" screen, the software requires that all the selected probes remain plugged into the generator, or else the software will display an error message (e.g. "Probe #2 unplugged", etc.), and will also force the user back to the "Probe Selection" screen. However, sometimes doctors may want to perform another scan of the lesion or perform some other procedure while leaving the probes inserted in the patient. But, if the procedure cannot be performed near the generator, the probes are unplugged from the generator. If the user selects the "UnDock Probes" button, this will allow the probes to be unplugged from the generator without causing an error message. Then, after the user has performed the other procedure that was required, he can re-attach the probes to the generator, and then select "Dock Probes" in input box 210. In this way, the user will not receive any error messages while the "Probe Placement Process" screen is displayed.

There is a default electric field density setting (Volts/cm) which is shown in input box 211. In the example, the default setting is 1500 Volts/cm. This number represents the electric field density that the user believes is needed to effectively treat the cells, e.g., ablate the tissue cells. For example, 1500 Volts/cm is an electric field density that is needed to irreversibly electroporate the tissue cells. Based on the number selected in input box 211, the treatment control module 54 automatically adjusts the voltage (treatment energy level) applied between the electrodes, as shown in column 222.

Box 280 allows a user to select between two different Volts/cm types, namely "Linear" or "Non-Linear Lookup".

The default Volts/cm setting is "Linear", in which case the Voltage that is applied between a given pair of electrodes, as shown in column 222, is determined by the following formula:

$$\text{Voltage} = xd, \qquad (1)$$

where x=the electric field density setting (Volts/cm) shown in column 225, which is based on the value from box 211, and where d=the distance (cm) between the given pair of electrodes shown in column 226.

Therefore, when "Linear" is selected, the Voltage that is applied between a given pair of electrodes is directly proportional to the Distance between the given electrode pair in a linear relationship.

If the user selects "Non-Linear Lookup" in box 280, then the Voltage that is applied between the given pair of electrodes will be similar to the Voltage values for a "Linear" selection when a pair of electrodes are closely spaced together (e.g. within about 1 cm). However, as a pair of given electrodes are spaced farther from one another, a "Non-Linear Lookup" will produce lower Voltages between the given pair of electrodes as compared to the Voltage values for a "Linear" selection at any given distance. The "Non-Linear Lookup" feature is particularly useful for reducing "popping" during treatment. "Popping" refers to an audible popping noise that sometimes occurs, which is believed to be caused by a plasma discharge from high voltage gradients at the tip of the electrodes. The "Non-Linear Lookup" feature can also minimize any swelling of the tissue that might occur as a result of a treatment. The Voltage values used for the "Non-Linear Lookup" selection can be pre-determined based on animal experiments and other research. In one embodiment, different tissue types can each have their own "Non-Linear Lookup" table. In the example shown, the tissue being treated is prostate tissue.

The details of the treatment parameters are displayed in window 270. The firing (switching) sequence between probes is listed automatically in window 270. In the example, the firing sequence involves six steps beginning with between probes 1 and 2, then probes 1 and 3, then probes 2 and 3, then probes 2 and 4, then probes 3 and 4, and then probes 4 and 1. As shown, the polarity of each of the probes may switch from negative to positive according to step of the firing sequence. Column 220 displays which probe is the positive probe (according to a number assigned to each probe) for each step. Column 221 displays which probe is the negative probe (according to a number assigned to each probe) for each step. Column 222 displays the actual voltage generated between each probe during each step of the firing sequence. In the example, the maximum voltage that can be generated between probes is limited by the capabilities of the generator 10, which in the example is limited to a maximum of 3000 Volts. Column 223 displays the length of each pulse that is generated between probes during each respective step of the firing sequence. In the example, the pulse length is predetermined and is the same for each respective step, and is set at 100 microseconds. Column 224 displays the number of pulses that is generated during each respective step of the firing sequence. In the example, the number of pulses is predetermined and is the same for each respective step, and is set at 90 pulses which are applied in a set of 10 pulses at a time. Column 225 displays the setting for Volts/cm according to the value selected at input box 211. Column 226 displays the actual distance between the electrodes (measured in cm), which is automatically calculated according to the placement of each probe in the grid 200.

The treatment control module 54 can be programmed to calculate and display the area of the combined treatment regions on the grid 200 by several different methods.

Each method determines a boundary line surrounding a treatment zone that is created between a pair of electrodes. By combining a plurality of treatment zones with each treatment zone being defined by a pair of electrodes, a combined treatment region can be displayed on the x-y grid.

Figure 6:
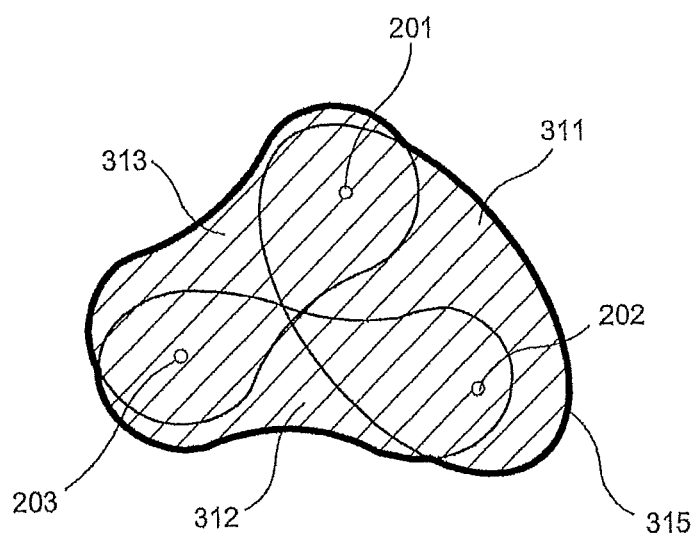
FIG. 6 illustrates an example of a three probe array defining three individual treatment zones, which combine to form a combined treatment region.

FIG. 6 illustrates three electrodes 201 (E1), 202 (E2), 203 (E3) defining three individual treatment zones 311, 312, 313, which combine to form a combined treatment region 315 which is shown with hatched lines.

As discussed above, the monitor can further include an x-z grid to illustrate the depth of the lesion and the shape of the treatment region. The shape of the treatment zone in the x-z grid will vary according to the selected amounts of electrode exposure for each probe and can be determined by one or more methods.

In one embodiment, the treatment boundary line that is created between two points on the x-y grid can be rotated about an axis joining the two points in order to generate the treatment region boundary line on the x-z grid. In this embodiment, several points may be selected along the exposed length of the active electrode portion for each probe at various depths (z). A three-dimensional combined treatment region can then be generated by determining the boundary line on the x-y grid between each individual pair of points and then rotating the boundary line along the axis joining each pair of points. The resulting boundary lines can be combined to create a three dimensional image that is displayed on the monitor.

The following is an alternate method for determining a boundary line on the x-z grid, thereby determining a three dimensional treatment region. This example describes a two probe array with the probes being inserted in a parallel relationship and with the probes having the same amount of exposed portions of the electrode. In this example, the exposed portions of each probe start at the same "uppermost" depth (z) and end at the same "lowermost" depth (z). First, a treatment zone boundary line is created in the x-y plane at the uppermost depth (z). Next, the treatment zone boundary line is repeatedly created stepwise for all subsequently lower depths (z), preferably evenly spaced, until the lowermost depth (z) is reached. The result is a 3-D volume (stacked set of treatment zone boundary lines) having a flat top surface and a flat bottom surface. Next, two new focus points are selected, with the first focus point positioned midway between the probe positions in the x-y grid and near the uppermost depth (z) of the exposed electrode. The second focus point is also positioned midway between the probe positions in the x-y grid, but near the lowermost depth (z) of the exposed electrode. Next, a treatment zone boundary line is created in the x-z grid using one of the methods described earlier. The actual placement of each focus point may be closer together, namely, not positioned in the uppermost and lowermost x-y planes defined by the exposed portions. The placement of each focus point should be selected so that the treatment zone boundary line that is created in the x-z grid closely matches the treatment zone boundary lines that were created in the uppermost and lowermost x-y grids. Next, the treatment zone boundary line that was created in the x-z grid according to the two focus points is rotated about the axis joining the two focus points. This creates the shapes for the upper and lower 3-D volumes which are added to the flat top surface and the flat bottom surface described above.

The above methods can be applied by persons of ordinary skill in the art to create 3-D treatment zones between exposed portions of electrodes even when the probes are not parallel to each other and even when the amount of the exposed portion varies with each probe.

Furthermore, there are situations where it is advantageous to show multiple boundary zones as a result of a therapy. For example, indicating which regimes undergo no change, reversible electroporation, irreversible electroporation, and conventional thermal damage is possible in accordance with the present invention. In addition, it is possible to output the entire distribution rather than just delineating boundaries.

It has been shown repeatedly in the literature that tissue properties are highly variable between tissue types, between individuals, and even within an individual. These changes may result from differences in body fat composition, hydration levels, and hormone cycles. Due to the large dependence of IRE (irreversible electroporation) treatments on tissue conductivity, it is imperative to have accurate values. Therefore, to obtain viable conductivity values prior to treatment, a low amplitude voltage pulse is used between the electrode conductors and the resultant impedance/conductance is measured as a way to determine pertinent tissue property data such as the predicted current. The value determined may then be implemented when assessing field strength and treatment protocol in real time. For example, the resulting impedance or predicted current can be used to set the default electric field density.

One method of generating an estimated treatment region between a pair of treatment electrodes is a numerical model based method involving finite element analysis (FEA). For example, U.S. Patent Application Publication No. 2007/0043345, which is hereby incorporated by reference, discloses using FEA models to generate treatment zones between a pair of electrodes (the calculations were performed using MATLAB's finite element solver, Femlab v2.2 (The MathWorks, Inc. Natick, Mass.)).

Most engineering problems can be solved by breaking the system into cells where each corner of the cell or mesh is a node. FEA is used to relate each node to each of the other nodes by applying sets of partial differential equations. This type of a system can be coded by scratch, but most people use one of many commercial FEA programs that automatically define the mesh and create the equations given the model geometry and boundary conditions. Some FEA programs only work in one area of engineering, for example, heat transfer and others are known as mulitphysics. These systems can convert electricity to heat and can be used for studying the relationships between different types of energy.

Typically the FEA mesh is not homogeneous and areas of transition have increased mesh density. The time and resources (memory) required to solve the FEA problem are proportional to the number of nodes, so it is generally unwise to have a uniformly small mesh over the entire model. If possible, FEA users also try to limit the analysis to 2D problems and/or use planes of symmetry to limit the size of the model being considered because even a modest 2D model often requires 30 minutes to several hours to run. By comparison, a 3D Model usually takes several hours to several days to run. A complicated model like a weather system or a crash simulation may take a super computer several days to complete.

Depending on the complexity of the FEA models that are required, the purchase price of the FEA modeling software can cost several thousand dollars for a low end system to $30 k for a non linear multiphysics system. The systems that model the weather are custom made and cost tens of millions of dollars.

In one example, the steps which are required for generating a treatment zone between a pair of treatment probes using finite element analysis include: (1) creating the geometry of interest (e.g., a plane of tissue with two circular electrodes); (2) defining the materials involved (e.g., tissue, metal); (3) defining the boundary conditions (e.g., Initial voltage, Initial temperature); (4) defining the system load (e.g., change the voltage of the electrodes to 3,000V); (5)

determining the type of solver that will be used; (6) determining whether to use a time response or steady state solution; (7) running the model and wait for the analysis to finish; and (8) displaying the results.

Using FEA, however, may not be practical for use in calculating and displaying in real time a treatment zone that is created between a pair of treatment probes in accordance with the present invention because of the time required to run these types of analyses. For the present invention, the system should allow a user to experiment with probe placement and should calculate a new treatment zone in less than a few seconds. Accordingly, the FEA model is not appropriate for such use and it would be desirable to find an analytic solution (closed form solution), which can calculate the treatment zones with only simple equations, but which closely approximate the solutions from a numerical model analysis such as the finite element analysis. The closed loop solutions should preferably generate the treatment zone calculation in a fraction of a second so as to allow a physician/user to experiment with probe placement in real time.

There are different closed loop (analytical model analysis) methods for estimating and displaying a treatment zone between a pair of treatment probes, which produce similar results to what would have been derived by a numerical model analysis such as FEA, but without the expense and time of performing FEA. Analytical models are mathematical models that have a closed form solution, i.e., the solution to the equations used to describe changes in a system can be expressed as a mathematical analytic function. The following method represents just one of the non-limiting examples of such alternative closed loop solutions.

In mathematics, a Cassini oval is a set (or locus) of points in the plane such that each point p on the oval bears a special relation to two other fixed points $q_1$ and $q_2$: the product of the distance from p to $q_1$ and the distance from p to $q_2$ is constant. That is, if the function dist(x,y) is defined to be the distance from a point x to a point y, then all points p on a Cassini oval satisfy the equation:

$$\text{dist}(q_1,p) \times \text{dist}(q_2,p) = b^2 \quad (2)$$

where b is a constant.

The points $q_1$ and $q_2$ are called the foci of the oval.

Suppose $q_1$ is the point (a, 0), and $q_2$ is the point (−a, 0). Then the points on the curve satisfy the equation:

$$((x-a)^2+y^2)((x+a)^2+y^2)=b^4 \quad (3)$$

The equivalent polar equation is:

$$r^4 - 2a^2 r^2 \cos 2\theta = b^4 - a^4 \quad (4)$$

The shape of the oval depends on the ratio b/a. When b/a is greater than 1, the locus is a single, connected loop. When b/a is less than 1, the locus comprises two disconnected loops. When b/a is equal to 1, the locus is a lemniscate of Bernoulli.

The Cassini equation provides a very efficient algorithm for plotting the boundary line of the treatment zone that was created between two probes on the grid 200. By taking pairs of probes for each firing sequence, the first probe is set as $q_1$ being the point (a, 0) and the second probe is set as $q_2$ being the point (−a, 0).

The polar equation for the Cassini curve is preferably used because it provides a more efficient equation for computation. The current algorithm can work equally as well by using the Cartesian equation of the Cassini curve. By solving for $r^2$ from eq. (4) above, the following polar equation was developed:

$$r^2 = a^2 \cos(2*\text{theta}) +/- \text{sqrt}(b^4 - a^4 \sin^2(2*\text{theta})) \quad (5)$$

where a=the distance from the origin (0, 0) to each probe in cm; and where b is calculated from the following equation:

$$b^2 = \left[\frac{V}{[\ln(a)(595.28)+2339]\left(\frac{A}{650}\right)}\right]^2 \quad (6)$$

where V=the Voltage (V) applied between the probes;

where a=the same a from eq. (5); and where A=the electric field density (V/cm) that is required to ablate the desired type of tissue according to known scientific values.

As can be seen from the mathematics involved in the equation, r can be up to four separate values for each given value for theta.

Example 1

If V=2495 Volts; a=0.7 cm; and A=650 V/cm;

Then $b^2$=1.376377 and then a cassini curve can be plotted by using eq. (5) above by solving for r, for each degree of theta from 0 degrees to 360 degrees.

A portion of the solutions for eq. (5) are shown in Table 1 below:

where M=$a^2$ cos(2*theta); and L=sqrt($b^4-a^4$ $\sin^2$(2*theta))

TABLE 1

| Theta (degrees) | r = sqrt(M + L) | r = −sqrt(M + L) | r = sqrt(M − L) | r = −sqrt(M − L) |
|---|---|---|---|---|
| 0 | 1.366154 | −1.36615 | 0 | 0 |
| 1 | 1.366006 | −1.36601 | 0 | 0 |
| 2 | 1.365562 | −1.36556 | 0 | 0 |
| 3 | 1.364822 | −1.36482 | 0 | 0 |
| 4 | 1.363788 | −1.36379 | 0 | 0 |
| 5 | 1.362461 | −1.36246 | 0 | 0 |
| 6 | 1.360843 | −1.36084 | 0 | 0 |
| 7 | 1.358936 | −1.35894 | 0 | 0 |
| 8 | 1.356743 | −1.35674 | 0 | 0 |
| 9 | 1.354267 | −1.35427 | 0 | 0 |
| 10 | 1.351512 | −1.35151 | 0 | 0 |
| 11 | 1.348481 | −1.34848 | 0 | 0 |
| 12 | 1.34518 | −1.34518 | 0 | 0 |
| 13 | 1.341611 | −1.34161 | 0 | 0 |
| 14 | 1.337782 | −1.33778 | 0 | 0 |
| 15 | 1.333697 | −1.3337 | 0 | 0 |

The above eq. (6) was developed according to the following analysis.

The curve from the cassini oval equation was calibrated as best as possible to the 650 V/cm contour line using two 1-mm diameter electrodes with an electrode spacing between 0.5-5 cm and an arbitrary applied voltage.

For this worksheet, $q_1$ and $q_2$ reference points (taken to be +/−electrodes) could be moved to locations along the x-axis to points of (±a, 0). A voltage could then be selected, and an arbitrary scaling factor ("gain denominator") would convert this voltage to the corresponding "b" used in eq. (4). The worksheet would then plot the resulting Cassini oval, which has a shape progression with applied voltage beginning as two circles around the electrodes that grow into irregular ellipses before converging into a single "peanut" shape that ultimately becomes an ellipse expanding from the original electrode locations.

The Cassini oval creates a reasonable visualization that mimics the shape of numerical results for the field distribution. In order to understand which values or levels correspond to a desired electric field of interest, a calibration involving the $b^4$ term was necessary to develop the relationship between the analytical Cassini oval and the numerical results. This was done through a backwards calibration process defined as follows:

1. A reference contour was selected to correlate the analytical and numerical solutions. This was chosen to be when b/a=1, forming a lemniscate of Bernoulli (the point where the two ellipses first connect, forming "∞").

2. A reference electric field density value was selected to be 650 V/cm.

3. Numerical models were developed to mimic the x-y output from the Cassini oval for scenarios where a=±0.25, 0.5, 0.75, 1.0, 1.25, 1.5, 1.75, 2.0, 2.25, and 2.5 cm.

4. Models were solved using trial and error to determine which voltage yielded the electric field contour of 650 V/cm in the shape of a lemniscate of Bernoulli.

5. The determined voltage was placed into the Cassini oval electronic worksheet for the same electrode geometry and the "gain denominator" was adjusted until the shape from the cassini oval matched that from the numerical solution.

6. The determined gain denominators for all values of "a" were collected and a calibration plot was made and fitted with a logarithmic trendline of:

$$\text{Gain Denominator} = 595.28 \cdot \ln(a) + 2339; \; R^2 = 0.993 \tag{7}$$

7. The calibration trendline function shown above was incorporated back into the Cassini Oval spreadsheet. At this point, the worksheet was capable of outputting a field contour of 650 V/cm for any electrode separation distance (±a) and applied voltage (V).

8. The calibration function was then scaled to a desired electric field contour input. This allowed the analytical solution to solve for any electric field for any given a separation distance and voltage. Since the Laplace equation is linear, scaling should provide a good estimate for how other fields would look.

Table 1 incorporates all the steps above to yield a single, calibrated Cassini Oval output that analytically predicts the electric field distribution; providing a quick and simple solution for the prediction of IRE (irreversible electroporation) treatment regions that may be adjusted in real-time. The inputs are the electrode location (as a given "±a" distance from the origin along the x-axis), the applied voltage to the energized electrode, and the desired electric field to visualize. The resulting output is a contour representing a threshold where the entire area within it has been subjected to an electric field≥the one selected; and thus treated by IRE. It is important to remember that the analytical solution was calibrated for an electric field contour of 650 V/cm, and thus yields an accurate approximation for this value. Other field strength contours of interest still yield reasonable results that mimic the overall shape of the electric field. Overall, the analytical solution provided yields consistently good predictions for electric field strengths, and thus, treatment regions of IRE that may be used during treatment planning or analysis.

A similar algorithm for calibration can be used for a bipolar electrode.

In one example, the diameter of the probe is 0.065 cm, and the lengths of the two electrodes are respectively 0.295 cm and 0.276 cm, separated by an insulation sleeve of 0.315 cm in length. Adapting this scenario to the cassini oval presents some challenges because the distribution is now resulting from the two exposed cylinder lengths, rather than two distinct loci of points. This was solved by calibrating individual electric field contours for the same applied voltage and developing two equations that adjust the separation distance (±a) and gain denominator (GD) according to the equations:

$$a = 7*10^{-9}*E^3 - 2*10^{-5}*E^2 + 0.015*E + 6.1619; \\ R^2 = 0.9806 \tag{8}$$

$$GD = 1.0121*E + 1920; \; R^2 = 0.9928 \tag{9}$$

where E is the electric field magnitude contour desired.

These two equations may then be used to calibrate the cassini ovals into a satisfactory shape to mimic the electric field distribution, and thus treatment region accordingly.

FIG. 6 illustrates an example of how to generate a combined treatment zone according to the invention. Three electrodes 201, 202, 203 defining three individual treatment zones 311, 312, 313, combine to form a combined treatment region 315 which is shown with hatched lines. By combining a plurality of treatment zones with each treatment zone being defined by a pair of electrodes, a combined treatment region 315 can be displayed on the x-y grid.

Figure 7:
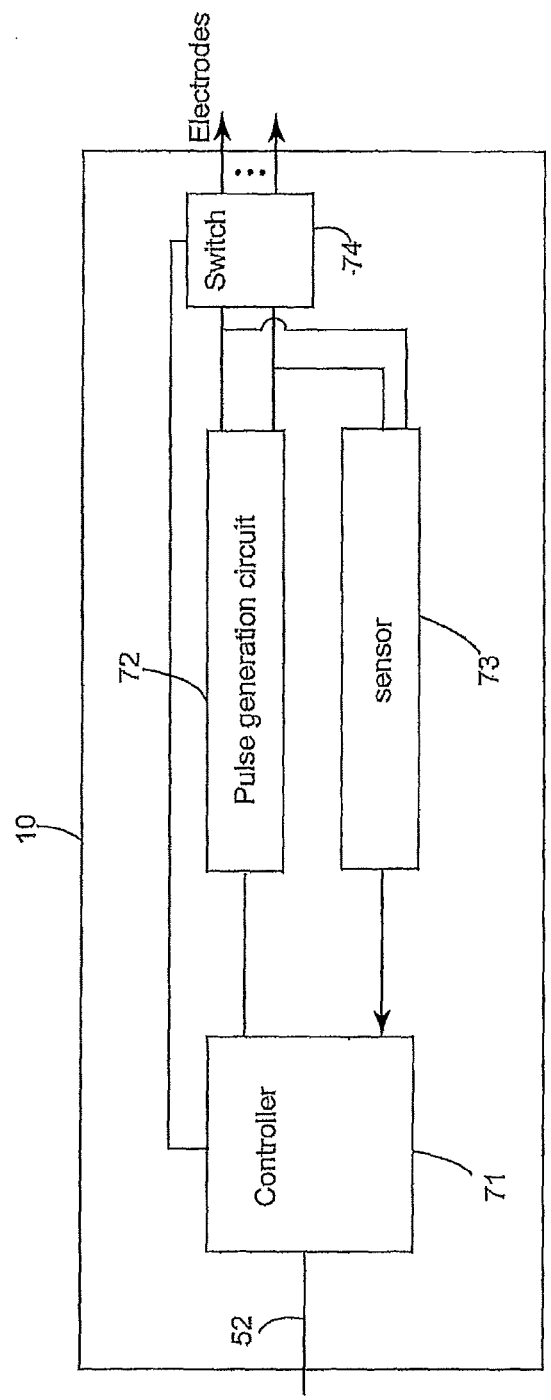
FIG. 7 illustrates details of the generator shown in FIG. 1.

FIG. 7 illustrates one embodiment of a pulse generator according to the present invention. A USB connection 52 carries instructions from the user computer 40 to a controller 71. The controller can be a computer similar to the computer 40 as shown in FIG. 2. The controller 71 can include a processor, ASIC (application-specific integrated circuit), microcontroller or wired logic. The controller 71 then sends the instructions to a pulse generation circuit 72. The pulse generation circuit 72 generates the pulses and sends electrical energy to the probes. In the embodiment shown, the pulses are applied one pair of electrodes at a time, and then switched to another pair using a switch 74, which is under the control of the controller 71. The switch 74 is preferably an electronic switch that switches the probe pairs based on the instructions received from the computer 40. A sensor 73 such as a sensor can sense the current or voltage between each pair of the probes in real time and communicate such information to the controller 71, which in turn, communicates the information to the computer 40. If the sensor 73 detects an abnormal condition during treatment such as a high current or low current condition, then it will communicate with the controller 71 and the computer 40 which may cause the controller to send a signal to the pulse generation circuit 72 to discontinue the pulses for that particular pair of probes.

The treatment control module 54 can further include a feature that tracks the treatment progress and provides the user with an option to automatically retreat for low or missing pulses, or over-current pulses (see discussion below). Also, if the generator stops prematurely for any reason, the treatment control module 54 can restart at the same point where it terminated, and administer the missing treatment pulses as part of the same treatment.

In other embodiments, the treatment control module 54 is able to detect certain errors during treatment, which include, but are not limited to, "charge failure", "hardware failure", "high current failure", and "low current failure".

According to the present invention, irreversible electroporation (IRE) ablation (n=81, where n is the number of IRE ablation procedures) was performed in-vivo in 22 pig livers using 2-4 IRE electrodes (18 gauge, 2 cm long tip) and a NanoKnife™ generator (AngioDynamics, Fremont, Calif.) as described in the IRE Treatment Application referenced above and as shown in FIGS. 1, 2 and 7. Cardiac-gated (i.e., synchronized to cardiac cycle) 100 μsec IRE pulses were applied sequentially between electrode pairs at 3,000-3,400V (one pair at a time).

Multiple variables for energy deposition and electrode configuration were studied including: inter-electrode spacing (1.5 cm-3 cm); the number of IRE pulses applied between electrode pairs (c=10, 50, & 100); and the order and number of times/cycles each electrode pair was activated.

For c=10, a sequence of delivered pulses are as follows: 10 sequential IRE pulses were delivered per electrode pair for all pairs (e.g., 10 pulses for pair 1-2, then 10 pulses for pair 2-3 and then 10 pulses for pair 3-1 for a 3-electrode array). Then the same sequence is repeated 2 to 44 times for a total number of IRE pulses delivered of 20 to 440 per electrode pair. Electrode phase (polarity) was changed after each sequence (1-2, 2-3, 3-1; 2-1, 3-2, 1-3), which reduces gas buildup near the electrodes to thereby reduce the chance of sparks. In one experiment, a total of 90 IRE pulses were delivered for each electrode pair.

For c=50, a sequence of 50 IRE pulses were delivered per electrode pair for all pairs. Then the same sequence is repeated one more time for a total number of IRE pulses delivered of 100 per electrode pair.

For c=100, a sequence of 100 sequential IRE pulses were delivered per each electrode pair. Then the same sequence is repeated one more time for a total number of IRE pulses delivered of 200 per electrode pair.

Between two pulses, two electrode pairs and two sequences, there is a waiting (delay) period. The reasons for the waiting period are to dissipate any thermal buildup in the tissue cells, especially around the electrodes where the current density is highest, and to increase the ablation zone.

Preferably, the generator 10 inserts a time delay between two pulses (inter-pulse delay) of at least 250 ms (milliseconds) and at most 15 seconds, and more preferably at least 1 second and at most 8 seconds. At greater than 8 seconds, the ablation zone does not increase and actually may help to decrease it.

Preferably, the generator 10 inserts a time delay of 5 seconds to 10 minutes between electrode pairs (inter-pair delay) within a sequence. Preferably, the generator inserts a time delay of 5 seconds to 20 minutes between two sequences (inter-sequence delay).

With a single IRE pulse, the cells try to close the holes/pores created in the membrane within a fraction of a second. By applying multiple pulses with inter-pulse, inter-pair and inter-sequence delays, it is believed that the cells' attempt to repeatedly close the holes exhaust their ability to close them, which thereby increases the ablation zone.

Ablations were performed under ultrasound guidance. Dimensions of resultant zones of treatment were measured by ultrasound 1-3 hr post-procedure and confirmed at gross and histopathology. These data and ablation times were compared and subject to statistical analysis to determine optimal pulse parameters.

Although the experiments involved 10, 50 and 100 pulses in a sequence, the general inventive concept can be expanded to include as little as 1 pulse per electrode pair in a sequence. In other words, for a 3 electrode array, a sequence of 1 IRE pulse per electrode pair is applied for all three pairs. Then, the sequence is repeated for 70 to 100 times. Preferably, the number of pulses for each electrode pair in a single sequence can vary between 1 and 280.

Currently, the NanoKnife™ generator is programmed to deliver a single IRE pulse per cardiac cycle if a cardiac-sync is selected. In a 3 or more multi-electrode array, more than one IRE pulse per cycle can be delivered by switching electrodes using the switch 74. For example, in a 3 electrode-array arrangement, in a single cardiac cycle, a sequence of single IRE pulse between pair 1-2, between pair 2-3 and between pair 2-3 can be applied for a total of 3 IRE pulses delivered, for example, within an R-wave of the cycle.

Alternatively, for applying 100 pulses, a sequence of 10 IRE pulses between pair 1-2, then between pair 2-3 and then between pair 2-3 can be applied for a total of 10 sets to deliver a total of 100 pulses for each electrode pair. For applying 500 pulses, a sequence of 10 IRE pulses can be sequentially applied to the 3 electrode pairs for a total of 50 sets. For applying 1000 pulses, a sequence of 10 IRE pulses can be sequentially applied to the 3 electrode pairs for a total of 100 sets.

The IRE pulses can be unipolar pulses or alternating polarity pulses such as biphasic pulses or consecutive positive and negative pulses separated by a slight time delay.

According to the experiments, the largest contiguous zones of treatment effect (6.4±0.6 cm width and length, 3.7±1.4 cm height) were achieved applying 2 cycles (sequences) of 50 IRE pulses sequentially to all electrode pairs within a 4 electrode array of 2.5 cm spacing (total time=17.5±6.7 min). For 4 electrode arrays, treatment diameter best correlated with overall time of the energy application [r2=0.71]). Greatest ablation for 3 electrode arrays (5.9±0.4 cm×5.3±0.5 cm cross-sectional area) was achieved by continuously delivering 10 pulses sequentially to each of the 3 electrode pairs for 10-12 min. For 2 electrode arrays using similar energy application strategies, ablation of only 3.9±0.5 cm length with variable width (incomplete to 2.4 cm) was achieved.

Figure 8:
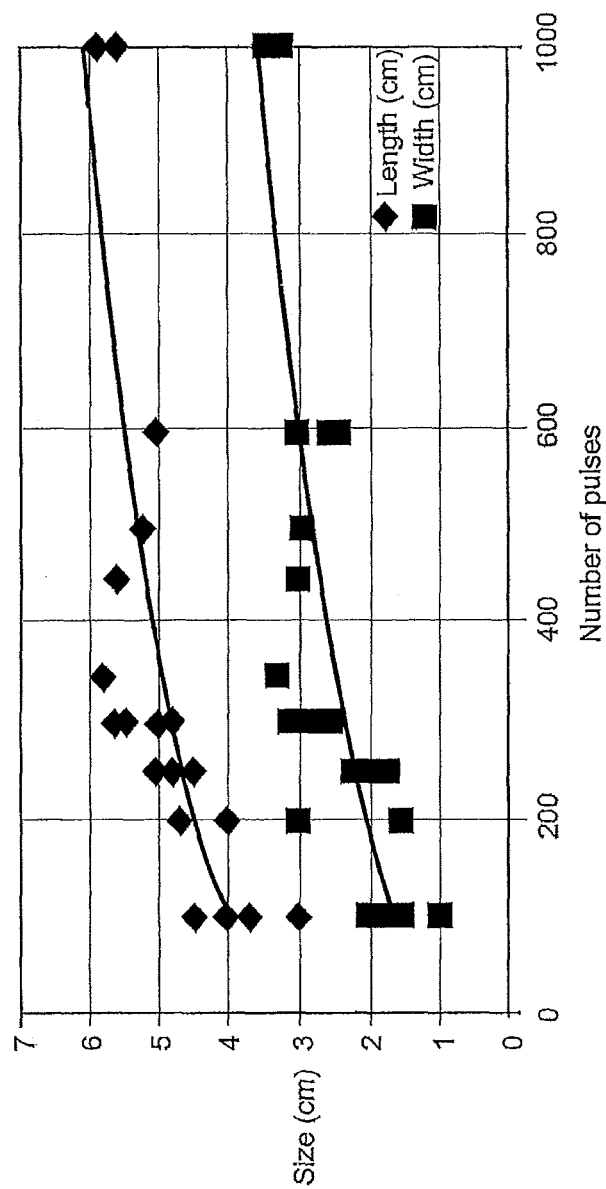
FIG. 8 is a graph illustrating the relationship of the number of pulses delivered and the size of the actual ablation region according to the present invention.

In another experiment, IRE ablation procedures were performed on porcine liver using the following parameters: 2.5 cm spacing between the electrodes, 100 μs pulses, 3 kVolts, 2 cm exposed electrodes, and 100-1000 pulses delivered. FIG. 8 is a graph illustrating the relationship of the number of pulses delivered to a pair of electrodes and the size of the actual ablation region in this experiment.

As can be seen, there is generally a positive correlation between the number of pulses (and therefore the total pulse application time) and the size of the ablation region although the rate of increase slows as more pulses are applied. For length, it varied between 4 cm and 5.7. For width, it varied between 1.5 cm and 3.3 cm. Using a curve fitting algorithm, the graph for length and width produced the following formulas:

$$y = 1.6832 * x^{0.1849},$$

where x=length in centimeter, and $$y = 0.3407 * x^{0.3381},$$

where x=width in centimeter.

Table 2 below summarizes the experimental data in terms of the increase in size in two dimensions (area) and three dimensions (volume).

TABLE 2

| # of 100 μs pulses | Width of ablated region (cm) | Length of ablated region (cm) | 2-D ablated region (cm^2) | % increase in area | 3-D ablated volume (cm^3) | % increase in volume |
|---|---|---|---|---|---|---|
| 100 | 1.5 | 4 | 6 | NA | 24 | NA |
| 600 | 2.9 | 5.5 | 15.95 | 166% | 87.725 | 266% |
| 1000 | 3.3 | 6 | 19.8 | 230% | 118.8 | 395% |

As seen above, for two dimensional regions, increasing the number of pulses from 100 to 600 and 1000 respectively produced a surprisingly large increase of 166% and 230% in ablation area. If an assumption is made that the increase in depth is similar to the increase in length, then increasing the number of pulses from 100 to 600 and 1000 respectively produces an increase of 266% and 395% in ablation volume.

Based on the above relationship between the ablation size and the number of delivered pulses, calculation of the estimated treatment region can be adjusted accordingly. For example, if the experimental data show that the shape of the treatment region increases proportionally (width, length and depth of the region), then the term $b^2$ in the Cassini oval equation may be adjusted accordingly. If, however, the shape of the treatment region increases in a non-proportional manner (e.g., length increases at twice the rate as the width), then the Cassini oval equation can be modified by adding or subtracting a constant to the $b^2$ term (e.g., $b^2+/-C$) as well as adjusting the $b^2$ term itself. Alternatively, the number of electrodes can be reduced.

Aside from varying the number of applied pulses, varying the width of each pulse from 20 microseconds to 100 microseconds produced a slight increase in the ablation size. Increasing the pulse width, however, also reduced the variance in ablation size (i.e., reduction in standard deviation). As the pulse width increased past 50-70 microseconds, the variance among the ablation sizes decreased substantially. This effect became more pronounced for longer spacing between the electrodes (e.g., greater than 3 cm). Thus, this information could also be used to increase the ablation size and also to more accurately predict the ablation size.

In procedures involving 3 or more electrodes, rather than applying the total number of electrodes sequentially for each pair, then moving on to the next pair, dividing up the total number of pulses to be delivered into smaller subsets and then applying each subset of pulses to each pair, and then repeating the sequence for the subsequent subsets while reversing the polarity for each sequence (i.e., E1(+)-E2(−), then E2(+)-E1(−) in the next sequence) produced an increase in the ablation size, especially when the total number of pulses for each pair was substantially higher than 100.

For a 3-electrode procedure and the total number of pulses=500, for example, the sequence of delivered pulses are as follows: 10 sequential IRE pulses per electrode pair for all pairs (e.g., 10 pulses for pair 1-2, then 10 pulses for pair 2-3 and then 10 pulses for pair 3-1). Then the same sequence is repeated 50 times for a total number of IRE pulses delivered of 500 per electrode pair with the electrode phase (polarity) being reversed after each sequence.

Figure 9:
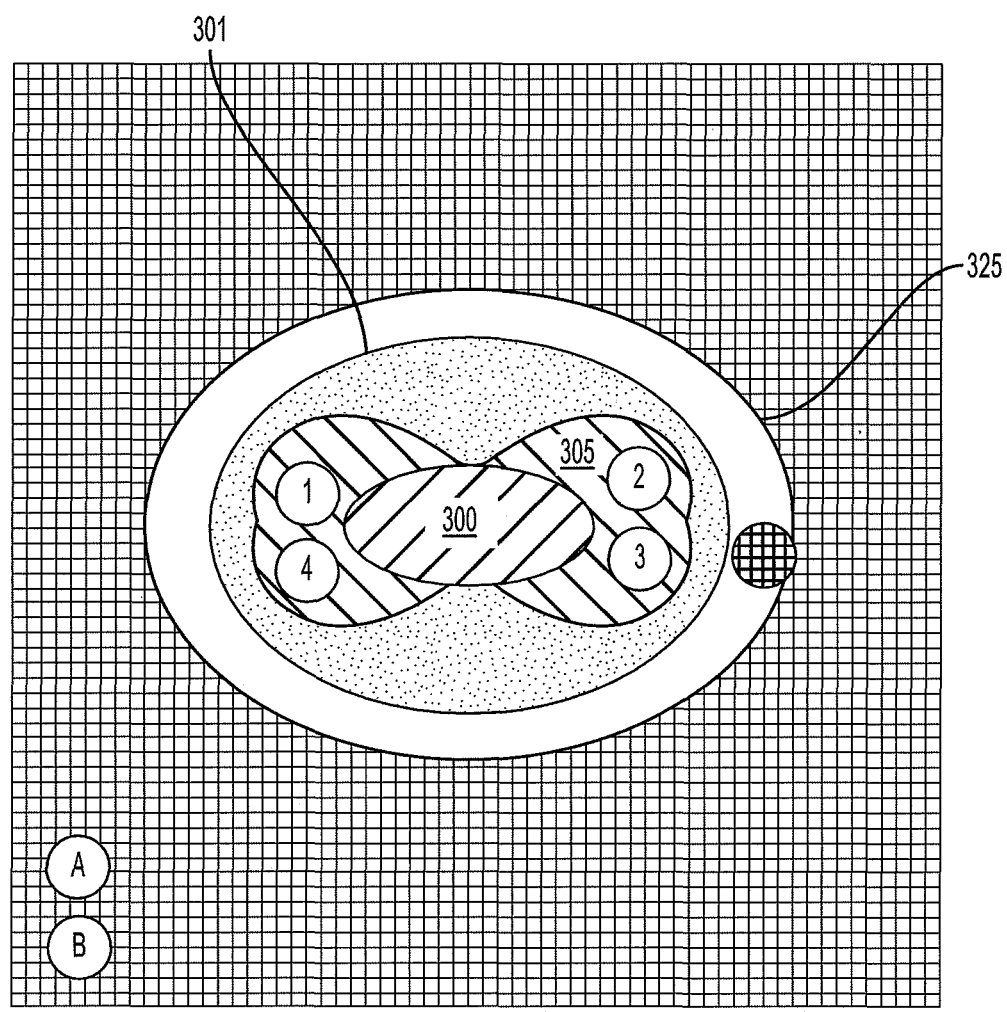
FIG. 9 illustrates ablation regions of varying sizes according to the number of pulses delivered according to the present invention.

FIG. 9 illustrates ablation regions of different sizes that are displayed on the monitor 11 according to the number of pulses delivered. The original lesion or target area 300 has been increased to an enlarged target region 301 which adds a margin of error. The estimated ablation area 305 has been generated assuming that 100 pulses will be delivered with four electrodes positioned as shown (superimposed over the target region 301). As can be seen, the estimated ablation/treatment area 305 barely covers the original target area 300 and is clearly inadequate to cover the enlarged target region 301.

However, according to the present invention, the enlarged target region 301 can be adequately covered by an increased ablation area 325 which has been calculated based on 1000 pulses (and which has been superimposed over the target region 301). Since such a large treatment area 325 can damage too much of good tissue, after receiving identification of a target region, the treatment control module 54 can select/adjust the number of pulses or number of electrodes, or both so that the resulting estimated treatment area sufficiently covers the target region 301 while minimizing ablation of good tissue. One way to do so is to generate a plurality of estimated ablation regions based on a plurality of pulse count, and then selecting the minimum pulse count that completely covers the target region 301 while minimizing damage to good tissue.

Advantageously, the present invention allows treatment of larger ablation regions with fewer electrodes to thereby provide a safer and less expensive electrical ablation procedure for patients. The present invention also allows treatment of a larger ablation area without dividing up the area into multiple regions and repeating the procedure.

The above disclosure is intended to be illustrative and not exhaustive. This description will suggest many modifications, variations, and alternatives may be made by ordinary skill in this art without departing from the scope of the invention. Those familiar with the art may recognize other equivalents to the specific embodiments described herein. Accordingly, the scope of the invention is not limited to the foregoing specification.

What is claimed is:

1. A system for planning a treatment of non-thermally and electrically ablating tissue of a patient through a plurality of electrodes comprising:
   a memory;
   a processor coupled to the memory;
   a display device connected to the processor, the display device displaying a user interface, the user interface allowing the user to input and change at least one treatment parameter;
   a treatment control module stored in the memory and executable by the processor, the treatment control module adapted to:
      receive parameters for a target ablation region;
      select a number of electrical pulses based on the target ablation region and the positions of the electrodes; and
      generate an estimated treatment region based on the number of electrical pulses to be applied through the electrodes the generated estimated treatment region displayed on the display prior to a treatment procedure, the estimated treatment region being a non-thermally ablated tissue region, altering the generated estimated treatment region by changing at least one treatment parameter on the user interface.

2. The system of claim 1, wherein the treatment control module further generates the estimated treatment region based on the number and positions of electrodes.

3. The system of claim 1, wherein the treatment control module further generates the treatment region based on the positions of the electrodes.

4. The system of claim 1, wherein the treatment control module displays on the display device a target ablation region superimposed with the generated estimated treatment region.

5. The system of claim 1, wherein the treatment control module:
   generates a plurality of estimated treatment regions based on different numbers of pulses to be applied; and
   selects an optimal number of pulses to be applied based on the generated treatment regions.

6. The system of claim 1, wherein the treatment control module:
   generates a plurality of estimated treatment regions based on different numbers of pulses to be applied and different numbers of electrodes; and
   selects an optimal number of electrodes to be applied and an optimal number of electrodes based on the generated treatment regions.

7. The system of claim 1, wherein the treatment control module selects a pulse width based on a target ablation region.

8. The system of claim 1, wherein the plurality of electrodes includes at least three electrodes (E1, E2 and E3), the system further comprising a pulse generator adapted to deliver, in sequence, at least one pulse to a first pair of electrodes (E1-E2), at least one pulse to a second pair of electrodes (E2-E3) and at least one other pulse to the first pair of electrodes (E1-E2).

9. The system of claim 1, wherein the plurality of electrodes includes at least three electrodes (E1, E2 and E3), the system further comprising a pulse generator, under the control of the treatment control module, adapted to deliver, in sequence, a set of pulses to a first pair of electrodes (E1-E2), a set of pulses to a second pair of electrodes (E2-E3), a set of pulses to a third pair of electrodes (E3-E1), and then repeat the same sequence of pulse delivery.

10. The system of claim 1, wherein the treatment control module further generates the estimated treatment region using a Cassini oval equation.

11. The system of claim 10, wherein treatment control module: further generates the estimated treatment region using the following Cassini oval equation or its equivalent Cartesian equation:

$$r2 = a2\ \cos(2*theta) +/- \mathrm{sqrt}(b4 - a4\ \sin 2(2*theta))$$

wherein a is the distance from the origin to each electrode and b is a constant; and adjusts the constant b based on the number of pulses to be applied.

12. The system of claim 1, wherein the treatment control module further generates the estimated treatment region according to a predetermined positive relationship between the number of pulses and the size of the ablation region.

13. The system of claim 1, wherein the treatment control module further generates the estimated treatment region according to a predetermined positive non-linear relationship between the number of pulses and the size of the ablation region.

14. The system of claim 1, wherein the treatment control module further generates the estimated treatment region according to a tissue conductivity of a tissue region of a patient to be treated.

15. The system of claim 1, wherein the treatment control module controls a pulse generator to generate two or more sequences of pulses in which an inter-sequence delay is greater than an inter-pulse delay within one sequence.

16. The system of claim 1, wherein the at least one treatment parameter changed is the depth of the plurality of electrodes.

* * * * *